United States Patent
Arbefeuille et al.

(10) Patent No.: US 9,101,506 B2
(45) Date of Patent: Aug. 11, 2015

(54) SYSTEM AND METHOD FOR DEPLOYING AN ENDOLUMINAL PROSTHESIS AT A SURGICAL SITE

(75) Inventors: Samuel Arbefeuille, Hollywood, FL (US); Fletcher Christian, Miami, FL (US); Joseph A. Manguno, Jr., Sunrise, FL (US); John C. Canning, Boynton Beach, FL (US)

(73) Assignee: Bolton Medical, Inc., Sunrise, FL (US)

( * ) Notice: Subject to any disclaimer, the term of this patent is extended or adjusted under 35 U.S.C. 154(b) by 372 days.

(21) Appl. No.: 12/723,431

(22) Filed: Mar. 12, 2010

(65) Prior Publication Data

US 2010/0234932 A1 Sep. 16, 2010

Related U.S. Application Data

(60) Provisional application No. 61/160,052, filed on Mar. 13, 2009, provisional application No. 61/255,339, filed on Oct. 27, 2009.

(51) Int. Cl.
*A61F 2/95* (2013.01)
*A61F 2/07* (2013.01)
*A61F 2/966* (2013.01)

(52) U.S. Cl.
CPC ... *A61F 2/95* (2013.01); *A61F 2/07* (2013.01); *A61F 2002/9505* (2013.01); *A61F 2002/9511* (2013.01); *A61F 2002/9665* (2013.01)

(58) Field of Classification Search
CPC ... A61F 2/95; A61F 2/966; A61F 2002/9505; A61F 2002/9511; A61F 2002/9522; A61F 2002/9528; A61F 2002/9534; A61F 2/954
USPC .................................. 606/108; 623/1.11, 1.12
See application file for complete search history.

(56) References Cited

U.S. PATENT DOCUMENTS 3,416,531 A  12/1968 Edwards
3,485,234 A  12/1969 Stevens
(Continued)

FOREIGN PATENT DOCUMENTS

CN    2451136 Y    10/2001
DE    197 53 123 A1    8/1999
(Continued)

OTHER PUBLICATIONS

Notification of Transmittal of the International Search Report and the Written Opinion of the International Searching Authority for Int'l Application No. PCT/US2010/027191; Date of Mailing: Sep. 29, 2010.
(Continued)

*Primary Examiner* — Christopher D Prone
(74) *Attorney, Agent, or Firm* — Hamilton, Brook, Smith & Reynolds, P.C.

(57) ABSTRACT

A system for implanting a prosthesis includes a control lumen and a nose cone affixed at a distal end of the control lumen. At least one supporting wire is affixed at one end, is substantially parallel to a major axis of the control lumen and is free at an opposite end, wherein the free end of at least one of the supporting wires is arcuate. Alternatively, a system for implanting a prosthesis includes at least one suture extending from a nose cone affixed to a distal end of a control lumen. The suture extends from the nose cone to a proximal end to a stent graft extending about the control lumen and from the stent graft to a fixed location on the control lumen. The suture is releasable from the stent graft by remote activation, whereby the suture separates from the nose cone to thereby deploy the stent graft.

35 Claims, 38 Drawing Sheets

(56) References Cited

U.S. PATENT DOCUMENTS

| | | | |
|---|---|---|---|
| 3,502,069 | A | 3/1970 | Silverman |
| 3,868,956 | A | 3/1975 | Alfidi et al. |
| 4,351,333 | A | 9/1982 | Lazarus et al. |
| 4,425,919 | A | 1/1984 | Alston, Jr. et al. |
| 4,487,808 | A | 12/1984 | Lambert |
| 4,515,593 | A | 5/1985 | Norton |
| 4,516,972 | A | 5/1985 | Samson |
| 4,534,363 | A | 8/1985 | Gold |
| 4,572,186 | A | 2/1986 | Gould et al. |
| 4,580,568 | A | 4/1986 | Gianturco |
| 4,634,432 | A | 1/1987 | Kocak |
| 4,655,771 | A | 4/1987 | Wallsten |
| 4,665,906 | A | 5/1987 | Jervis |
| 4,665,918 | A | 5/1987 | Garza et al. |
| 4,705,511 | A | 11/1987 | Kocak |
| 4,787,899 | A | 11/1988 | Lazarus |
| 4,817,613 | A | 4/1989 | Jaraczewski et al. |
| 4,990,151 | A | 2/1991 | Wallsten |
| 5,019,057 | A | 5/1991 | Truckai |
| 5,041,126 | A | 8/1991 | Gianturco |
| 5,057,092 | A | 10/1991 | Webster, Jr. |
| 5,067,957 | A | 11/1991 | Jervis |
| 5,104,399 | A | 4/1992 | Lazarus |
| 5,158,543 | A | 10/1992 | Lazarus |
| 5,176,660 | A | 1/1993 | Truckai |
| 5,201,757 | A | 4/1993 | Heyn et al. |
| 5,209,295 | A * | 5/1993 | Campos et al. ............... 166/303 |
| 5,254,105 | A | 10/1993 | Haaga |
| 5,282,824 | A | 2/1994 | Gianturco |
| 5,290,295 | A | 3/1994 | Querals et al. |
| 5,292,331 | A | 3/1994 | Boneau |
| 5,324,306 | A | 6/1994 | Makower et al. |
| 5,334,168 | A | 8/1994 | Hemmer |
| 5,338,295 | A | 8/1994 | Cornelius et al. |
| 5,342,384 | A | 8/1994 | Sugarbaker |
| 5,358,493 | A | 10/1994 | Schweich, Jr. et al. |
| 5,380,304 | A | 1/1995 | Parker |
| 5,387,235 | A | 2/1995 | Chuter |
| 5,397,345 | A | 3/1995 | Lazarus |
| 5,405,377 | A | 4/1995 | Cragg |
| 5,415,664 | A | 5/1995 | Pinchuk |
| 5,433,723 | A | 7/1995 | Lindenberg et al. |
| 5,456,713 | A | 10/1995 | Chuter |
| 5,458,615 | A | 10/1995 | Klemm et al. |
| 5,464,449 | A | 11/1995 | Ryan et al. |
| 5,474,563 | A * | 12/1995 | Myler et al. .................. 606/108 |
| 5,480,423 | A | 1/1996 | Ravenscroft et al. |
| 5,489,295 | A | 2/1996 | Piplani et al. |
| 5,507,771 | A | 4/1996 | Gianturco |
| 5,522,881 | A | 6/1996 | Lentz |
| 5,522,882 | A | 6/1996 | Gaterud et al. |
| 5,531,715 | A | 7/1996 | Engelson et al. |
| 5,533,987 | A | 7/1996 | Pray et al. |
| 5,534,007 | A | 7/1996 | St. Germain et al. |
| 5,540,712 | A | 7/1996 | Kleshinski et al. |
| 5,545,210 | A | 8/1996 | Hess et al. |
| 5,562,726 | A | 10/1996 | Chuter |
| 5,562,728 | A | 10/1996 | Lazarus et al. |
| 5,569,218 | A | 10/1996 | Berg |
| 5,571,135 | A | 11/1996 | Fraser et al. |
| 5,575,816 | A | 11/1996 | Rudnick et al. |
| 5,575,817 | A | 11/1996 | Martin |
| 5,582,614 | A | 12/1996 | Feingold |
| 5,591,195 | A | 1/1997 | Taheri et al. |
| 5,597,378 | A | 1/1997 | Jervis |
| 5,601,568 | A | 2/1997 | Chevillon et al. |
| 5,607,442 | A | 3/1997 | Fischell et al. |
| 5,609,625 | A | 3/1997 | Piplani et al. |
| 5,609,627 | A | 3/1997 | Goicoechea et al. |
| 5,613,974 | A | 3/1997 | Andreas et al. |
| 5,618,270 | A | 4/1997 | Orejola |
| 5,628,754 | A | 5/1997 | Shevlin et al. |
| 5,628,783 | A | 5/1997 | Quiachon et al. |
| 5,632,763 | A | 5/1997 | Glastra |
| 5,639,278 | A | 6/1997 | Dereume et al. |
| 5,658,263 | A | 8/1997 | Dang et al. |
| 5,662,675 | A | 9/1997 | Polanskyj Stockert et al. |
| 5,662,700 | A | 9/1997 | Lazarus |
| 5,674,208 | A | 10/1997 | Berg et al. |
| 5,676,696 | A | 10/1997 | Marcade |
| 5,683,449 | A | 11/1997 | Marcade |
| 5,693,086 | A | 12/1997 | Goicoechea et al. |
| 5,700,269 | A | 12/1997 | Pinchuk et al. |
| 5,707,376 | A | 1/1998 | Kavteladze et al. |
| 5,709,703 | A | 1/1998 | Lukic et al. |
| 5,713,917 | A | 2/1998 | Leonhardt et al. |
| 5,716,365 | A | 2/1998 | Goicoechea et al. |
| 5,716,393 | A | 2/1998 | Lindenberg et al. |
| 5,720,776 | A | 2/1998 | Chuter et al. |
| 5,723,003 | A | 3/1998 | Winston et al. |
| 5,730,733 | A | 3/1998 | Mortier et al. |
| 5,733,267 | A | 3/1998 | Del Toro |
| 5,735,859 | A | 4/1998 | Fischell et al. |
| 5,749,921 | A | 5/1998 | Lenker et al. |
| 5,755,778 | A | 5/1998 | Kleshinski |
| 5,776,142 | A | 7/1998 | Gunderson |
| 5,782,811 | A | 7/1998 | Samson et al. |
| 5,782,904 | A | 7/1998 | White et al. |
| 5,782,909 | A | 7/1998 | Quiachon et al. |
| 5,788,707 | A | 8/1998 | Del Toro et al. |
| 5,792,144 | A | 8/1998 | Fischell et al. |
| 5,800,515 | A | 9/1998 | Nadal et al. |
| 5,800,517 | A | 9/1998 | Anderson et al. |
| 5,800,520 | A | 9/1998 | Fogarty et al. |
| 5,824,036 | A | 10/1998 | Lauterjung |
| 5,824,037 | A | 10/1998 | Fogarty et al. |
| 5,824,039 | A | 10/1998 | Piplani et al. |
| 5,824,040 | A | 10/1998 | Cox et al. |
| 5,824,041 | A | 10/1998 | Lenker et al. |
| 5,824,042 | A | 10/1998 | Lombardi et al. |
| 5,824,044 | A | 10/1998 | Quiachon et al. |
| 5,843,158 | A | 12/1998 | Lenker et al. |
| 5,843,160 | A | 12/1998 | Rhodes |
| 5,843,164 | A | 12/1998 | Frantzen et al. |
| 5,843,167 | A | 12/1998 | Dwyer et al. |
| 5,851,228 | A | 12/1998 | Pinheiro |
| 5,860,998 | A | 1/1999 | Robinson et al. |
| 5,871,536 | A | 2/1999 | Lazarus |
| 5,891,110 | A | 4/1999 | Larson et al. |
| 5,891,114 | A | 4/1999 | Chien et al. |
| 5,893,868 | A | 4/1999 | Hanson et al. |
| 5,899,892 | A | 5/1999 | Mortier et al. |
| 5,902,334 | A | 5/1999 | Dwyer et al. |
| 5,904,713 | A | 5/1999 | Leschinsky |
| 5,906,619 | A | 5/1999 | Olson et al. |
| 5,910,101 | A | 6/1999 | Andrews et al. |
| 5,911,715 | A | 6/1999 | Berg et al. |
| 5,916,263 | A | 6/1999 | Goicoechea et al. |
| 5,938,696 | A | 8/1999 | Goicoechea et al. |
| 5,944,726 | A | 8/1999 | Blacser et al. |
| 5,947,939 | A | 9/1999 | Mortier et al. |
| 5,951,495 | A | 9/1999 | Berg et al. |
| 5,954,651 | A | 9/1999 | Berg et al. |
| 5,957,949 | A | 9/1999 | Leonhardt et al. |
| 5,961,511 | A | 10/1999 | Mortier et al. |
| 5,968,069 | A | 10/1999 | Dusbabek et al. |
| 5,984,955 | A | 11/1999 | Wisselink |
| 5,993,481 | A | 11/1999 | Marcade et al. |
| 6,004,310 | A | 12/1999 | Bardsley et al. |
| 6,004,328 | A | 12/1999 | Solar |
| 6,004,347 | A | 12/1999 | McNamara et al. |
| 6,019,778 | A | 2/2000 | Wilson et al. |
| 6,024,763 | A | 2/2000 | Lenker et al. |
| 6,039,749 | A | 3/2000 | Marin et al. |
| 6,039,758 | A | 3/2000 | Quiachon et al. |
| 6,039,759 | A | 3/2000 | Carpentier et al. |
| 6,045,557 | A | 4/2000 | White et al. |
| 6,051,020 | A | 4/2000 | Goicoechea et al. |
| 6,053,943 | A | 4/2000 | Edwin et al. |
| 6,063,112 | A | 5/2000 | Sgro |
| 6,071,307 | A | 6/2000 | Rhee et al. |
| 6,099,548 | A | 8/2000 | Taheri |
| 6,099,558 | A | 8/2000 | White et al. |
| 6,099,559 | A | 8/2000 | Nolting |

(56) References Cited

U.S. PATENT DOCUMENTS

| | | | |
|---|---|---|---|
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,152,944 A | 11/2000 | Holman et al. |
| 6,165,163 A | 12/2000 | Chien et al. |
| 6,165,213 A | 12/2000 | Goicoechea et al. |
| 6,168,616 B1 | 1/2001 | Brown, III |
| 6,168,623 B1 | 1/2001 | Fogarty et al. |
| 6,183,481 B1 | 2/2001 | Lee et al. |
| 6,183,505 B1 | 2/2001 | Mohn, Jr. et al. |
| 6,183,506 B1 | 2/2001 | Penn et al. |
| 6,193,705 B1 | 2/2001 | Mortier et al. |
| 6,200,336 B1 | 3/2001 | Pavcnik et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,435 B1 | 4/2001 | Piplani et al. |
| 6,212,422 B1 | 4/2001 | Berg et al. |
| 6,213,976 B1 | 4/2001 | Trerotola |
| 6,214,038 B1 | 4/2001 | Piplani et al. |
| 6,221,079 B1 | 4/2001 | Magovern et al. |
| 6,221,102 B1 | 4/2001 | Baker et al. |
| 6,224,609 B1 | 5/2001 | Ressemann et al. |
| 6,228,063 B1 | 5/2001 | Aboul-Hosn |
| 6,231,601 B1 | 5/2001 | Myers et al. |
| 6,238,430 B1 | 5/2001 | Klumb et al. |
| 6,245,052 B1 | 6/2001 | Orth et al. |
| 6,248,112 B1 | 6/2001 | Gambale et al. |
| 6,248,116 B1 | 6/2001 | Chevillon et al. |
| 6,251,132 B1 | 6/2001 | Ravenscroft et al. |
| 6,254,609 B1 | 7/2001 | Vrba et al. |
| 6,267,775 B1 | 7/2001 | Clerc et al. |
| 6,270,521 B1 | 8/2001 | Fischell et al. |
| 6,273,909 B1 | 8/2001 | Kugler et al. |
| 6,280,466 B1 | 8/2001 | Kugler et al. |
| 6,280,467 B1 | 8/2001 | Leonhardt |
| 6,287,315 B1 | 9/2001 | Wijeratne et al. |
| 6,302,906 B1 | 10/2001 | Goicoechea et al. |
| 6,302,907 B1 | 10/2001 | Hijlkema |
| 6,306,141 B1 | 10/2001 | Jervis |
| 6,312,458 B1 | 11/2001 | Golds |
| 6,319,275 B1 | 11/2001 | Lashinski et al. |
| 6,319,278 B1 | 11/2001 | Quinn |
| 6,322,585 B1 | 11/2001 | Khosravi et al. |
| 6,334,869 B1 | 1/2002 | Leonhardt et al. |
| 6,338,709 B1 | 1/2002 | Geoffrion et al. |
| 6,342,066 B1 | 1/2002 | Toro et al. |
| 6,344,044 B1 | 2/2002 | Fulkerson et al. |
| 6,344,052 B1 | 2/2002 | Greenan et al. |
| 6,346,118 B1 | 2/2002 | Baker et al. |
| 6,350,278 B1 * | 2/2002 | Lenker et al. ............... 623/1.12 |
| 6,355,056 B1 | 3/2002 | Pinhciro |
| 6,355,060 B1 | 3/2002 | Lenker et al. |
| 6,368,345 B1 | 4/2002 | Dehdashtian et al. |
| 6,375,675 B2 | 4/2002 | Dehdashtian et al. |
| 6,375,676 B1 | 4/2002 | Cox |
| 6,379,372 B1 | 4/2002 | Dehdashtian et al. |
| 6,389,946 B1 | 5/2002 | Frid et al. |
| 6,395,017 B1 | 5/2002 | Dwyer et al. |
| 6,395,022 B1 | 5/2002 | Piplani et al. |
| 6,402,781 B1 | 6/2002 | Langberg et al. |
| 6,416,542 B1 | 7/2002 | Marcade et al. |
| 6,419,686 B1 | 7/2002 | McLeod et al. |
| 6,425,898 B1 | 7/2002 | Wilson et al. |
| 6,443,979 B1 | 9/2002 | Stalker et al. |
| 6,443,980 B1 | 9/2002 | Wang et al. |
| 6,450,988 B1 | 9/2002 | Bradshaw |
| 6,451,053 B1 | 9/2002 | Dehdashtian et al. |
| 6,454,796 B1 | 9/2002 | Barkman et al. |
| 6,458,867 B1 | 10/2002 | Wang et al. |
| 6,464,684 B1 | 10/2002 | Galdonik |
| 6,464,719 B2 | 10/2002 | Jayaraman |
| 6,464,721 B1 | 10/2002 | Marcade et al. |
| 6,478,818 B1 | 11/2002 | Taheri |
| 6,488,700 B2 | 12/2002 | Klumb et al. |
| 6,503,274 B1 | 1/2003 | Howanec, Jr. et al. |
| 6,505,066 B2 | 1/2003 | Berg et al. |
| 6,514,282 B1 | 2/2003 | Inoue |
| 6,517,571 B1 | 2/2003 | Brauker et al. |
| 6,517,572 B2 | 2/2003 | Kugler et al. |
| 6,517,573 B1 | 2/2003 | Pollock et al. |
| 6,520,951 B1 | 2/2003 | Carrillo, Jr. et al. |
| 6,520,986 B2 | 2/2003 | Martin et al. |
| 6,524,335 B1 | 2/2003 | Hartley et al. |
| 6,524,336 B1 | 2/2003 | Papazolgou et al. |
| 6,533,753 B1 | 3/2003 | Haarstad et al. |
| 6,540,698 B1 | 4/2003 | Ishii |
| 6,540,778 B1 | 4/2003 | Quiachon et al. |
| 6,551,350 B1 | 4/2003 | Thornton et al. |
| 6,562,022 B2 | 5/2003 | Hoste et al. |
| 6,565,596 B1 | 5/2003 | White et al. |
| 6,565,597 B1 | 5/2003 | Fearnot et al. |
| 6,575,994 B1 | 6/2003 | Marin et al. |
| 6,576,007 B2 | 6/2003 | Dehdashtian et al. |
| 6,582,458 B1 | 6/2003 | White et al. |
| 6,582,460 B1 | 6/2003 | Cryer |
| 6,592,526 B1 | 7/2003 | Lenker |
| 6,613,073 B1 | 9/2003 | White et al. |
| 6,616,626 B2 | 9/2003 | Crank et al. |
| 6,620,126 B2 | 9/2003 | Unsworth et al. |
| 6,641,606 B2 | 11/2003 | Ouriel et al. |
| 6,652,571 B1 | 11/2003 | White et al. |
| 6,652,572 B2 | 11/2003 | Kugler et al. |
| 6,660,033 B1 | 12/2003 | Marcade et al. |
| 6,676,666 B2 | 1/2004 | Vrba et al. |
| 6,682,536 B2 | 1/2004 | Vardi et al. |
| 6,682,537 B2 | 1/2004 | Ouriel et al. |
| 6,682,557 B1 | 1/2004 | Quiachon et al. |
| 6,685,736 B1 | 2/2004 | White et al. |
| 6,689,152 B2 | 2/2004 | Balceta et al. |
| 6,689,158 B1 | 2/2004 | White et al. |
| 6,692,458 B2 | 2/2004 | Forman et al. |
| 6,692,483 B2 | 2/2004 | Vardi et al. |
| 6,692,512 B2 | 2/2004 | Jang |
| 6,695,875 B2 | 2/2004 | Stelter et al. |
| 6,706,033 B1 | 3/2004 | Martinez et al. |
| 6,726,712 B1 | 4/2004 | Raeder-Devens et al. |
| 6,733,519 B2 | 5/2004 | Lashinski et al. |
| 6,733,523 B2 | 5/2004 | Shaolian et al. |
| 6,755,856 B2 | 6/2004 | Fierens et al. |
| 6,761,731 B2 | 7/2004 | Majercak |
| 6,790,222 B2 | 9/2004 | Kugler et al. |
| 6,802,860 B2 | 10/2004 | Cosgrove et al. |
| 6,808,529 B2 | 10/2004 | Fulkerson |
| 6,811,559 B2 | 11/2004 | Thornton |
| 6,814,748 B1 | 11/2004 | Baker et al. |
| 6,821,291 B2 | 11/2004 | Bolea et al. |
| 6,827,710 B1 | 12/2004 | Mooney et al. |
| 6,827,711 B2 | 12/2004 | Sunseri |
| 6,830,575 B2 | 12/2004 | Stenzel et al. |
| 6,843,803 B2 | 1/2005 | Ryan et al. |
| 6,849,084 B2 | 2/2005 | Rabkin et al. |
| 6,849,088 B2 | 2/2005 | Dehdashtian et al. |
| 6,858,034 B1 | 2/2005 | Hijlkema et al. |
| 6,859,986 B2 | 3/2005 | Jackson et al. |
| 6,860,901 B1 | 3/2005 | Baker et al. |
| 6,863,668 B2 | 3/2005 | Gillespie et al. |
| 6,866,660 B2 | 3/2005 | Garabedian et al. |
| 6,871,085 B2 | 3/2005 | Sommer |
| 6,884,260 B2 | 4/2005 | Kugler et al. |
| 6,890,348 B2 | 5/2005 | Sydney et al. |
| 6,911,039 B2 | 6/2005 | Shiu et al. |
| 6,916,335 B2 | 7/2005 | Kanji |
| 6,918,925 B2 | 7/2005 | Tehrani |
| 6,932,829 B2 | 8/2005 | Majercak |
| 6,938,646 B2 | 9/2005 | Litton |
| 6,939,371 B2 | 9/2005 | Kugler et al. |
| 6,945,989 B1 | 9/2005 | Betelia et al. |
| 6,945,990 B2 | 9/2005 | Greenan |
| 6,964,679 B1 | 11/2005 | Marcade et al. |
| 6,989,024 B2 | 1/2006 | Hebert et al. |
| 6,994,722 B2 | 2/2006 | DiCarlo |

(56) References Cited

U.S. PATENT DOCUMENTS

| | | |
|---|---|---|
| 7,001,420 B2 | 2/2006 | Speck et al. |
| 7,011,647 B2 | 3/2006 | Purdy et al. |
| 7,014,653 B2 | 3/2006 | Ouriel |
| 7,025,773 B2 | 4/2006 | Gittings et al. |
| 7,052,511 B2 | 5/2006 | Weldon et al. |
| 7,070,582 B2 | 7/2006 | Freyman et al. |
| 7,105,016 B2 | 9/2006 | Shiu et al. |
| 7,112,217 B1 | 9/2006 | Kugler et al. |
| 7,115,134 B2 | 10/2006 | Chambers |
| 7,125,419 B2 | 10/2006 | Sequin et al. |
| 7,147,660 B2 | 12/2006 | Chobotov et al. |
| 7,160,318 B2 | 1/2007 | Greenberg et al. |
| 7,163,552 B2 | 1/2007 | Diaz |
| 7,166,125 B1 | 1/2007 | Baker et al. |
| 7,169,170 B2 | 1/2007 | Widenhouse |
| 7,195,639 B2 | 3/2007 | Quiachon et al. |
| 7,225,518 B2 | 6/2007 | Eidenschink et al. |
| 7,238,197 B2 | 7/2007 | Sequin et al. |
| 7,264,632 B2 | 9/2007 | Wright et al. |
| 7,294,147 B2 | 11/2007 | Hartley |
| 7,351,256 B2 | 4/2008 | Hojeibane et al. |
| 7,708,771 B2 | 5/2010 | Chuter et al. |
| 7,717,950 B2 | 5/2010 | Greenan |
| 7,722,663 B1 | 5/2010 | Austin |
| 7,763,063 B2 | 7/2010 | Arbefeuille et al. |
| 7,766,962 B1 | 8/2010 | Quinn |
| 8,043,354 B2 | 10/2011 | Greenberg et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,292,943 B2 | 10/2012 | Berra et al. |
| 8,308,790 B2 | 11/2012 | Arbefeuille et al. |
| 8,449,595 B2 | 5/2013 | Ouellette et al. |
| 8,500,792 B2 | 8/2013 | Berra |
| 8,579,963 B2 | 11/2013 | Tabor |
| 8,636,788 B2 | 1/2014 | Arbefeuille et al. |
| 8,734,501 B2 | 5/2014 | Hartley et al. |
| 8,740,963 B2 | 6/2014 | Arbefeuille et al. |
| 2001/0000801 A1 | 5/2001 | Miller et al. |
| 2001/0001833 A1 | 5/2001 | Ravenscroft et al. |
| 2001/0034549 A1 | 10/2001 | Bartholf et al. |
| 2001/0049547 A1 | 12/2001 | Moore |
| 2002/0007193 A1 | 1/2002 | Tanner et al. |
| 2002/0013617 A1 | 1/2002 | Matsutani et al. |
| 2002/0016597 A1 | 2/2002 | Dwyer et al. |
| 2002/0016627 A1 | 2/2002 | Golds |
| 2002/0035394 A1 | 3/2002 | Fierens |
| 2002/0045929 A1 | 4/2002 | Diaz |
| 2002/0052660 A1 | 5/2002 | Greenhalgh |
| 2002/0072755 A1 | 6/2002 | Bigus et al. |
| 2002/0082523 A1 | 6/2002 | Kinsella et al. |
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0188344 A1 | 12/2002 | Bolea |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0088305 A1 | 5/2003 | Van Schie et al. |
| 2003/0135259 A1 | 7/2003 | Simso |
| 2003/0135269 A1 | 7/2003 | Swanstrom |
| 2003/0139803 A1 | 7/2003 | Sequin et al. |
| 2003/0163193 A1 | 8/2003 | Widenhouse |
| 2003/0176911 A1 | 9/2003 | Iancea et al. |
| 2003/0199966 A1 | 10/2003 | Shiu et al. |
| 2003/0212431 A1 | 11/2003 | Brady et al. |
| 2003/0220682 A1 | 11/2003 | Kujawski |
| 2003/0236564 A1 | 12/2003 | Majercak |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1 | 5/2004 | Wright et al. |
| 2004/0098084 A1 | 5/2004 | Hartley et al. |
| 2004/0106974 A1 | 6/2004 | Greenberg et al. |
| 2004/0117003 A1 | 6/2004 | Ouriel et al. |
| 2004/0148007 A1 | 7/2004 | Jackson et al. |
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193252 A1 | 9/2004 | Perez |
| 2004/0199240 A1 | 10/2004 | Dorn et al. |
| 2004/0230286 A1 | 11/2004 | Moore et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0033406 A1 | 2/2005 | Barnhart et al. |
| 2005/0038495 A1 | 2/2005 | Greenan |
| 2005/0049667 A1 | 3/2005 | Arbefeuille et al. |
| 2005/0049674 A1 | 3/2005 | Berra et al. |
| 2005/0080476 A1 | 4/2005 | Gunderson et al. |
| 2005/0080477 A1 | 4/2005 | Sydney et al. |
| 2005/0096726 A1 | 5/2005 | Sequin et al. |
| 2005/0107862 A1 | 5/2005 | Ohlenschlaeger |
| 2005/0149166 A1 | 7/2005 | Schaeffer et al. |
| 2005/0159803 A1 | 7/2005 | Lad et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0283223 A1 | 12/2005 | Greenan |
| 2006/0020319 A1 | 1/2006 | Kim et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |
| 2006/0135961 A1 | 6/2006 | Rosenman et al. |
| 2006/0178726 A1 | 8/2006 | Douglas |
| 2006/0178733 A1 | 8/2006 | Pinchuk et al. |
| 2006/0188408 A1 | 8/2006 | Arbefeuille et al. |
| 2006/0195172 A1 | 8/2006 | Luo et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2006/0276872 A1 | 12/2006 | Arbefeuille et al. |
| 2006/0282150 A1 | 12/2006 | Olson et al. |
| 2007/0048348 A1 | 3/2007 | Atanasoska et al. |
| 2007/0053952 A1 | 3/2007 | Chen et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100422 A1 | 5/2007 | Shumer et al. |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1* | 6/2007 | Moore et al. .................. 623/1.13 |
| 2007/0142894 A1 | 6/2007 | Moore et al. |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0168014 A1 | 7/2007 | Jimenez et al. |
| 2007/0173929 A1 | 7/2007 | Boucher et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0198078 A1 | 8/2007 | Berra et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |

(56) References Cited

U.S. PATENT DOCUMENTS

| | | |
|---|---|---|
| 2008/0021538 A1 | 1/2008 | Wright et al. |
| 2008/0046065 A1 | 2/2008 | Hartley et al. |
| 2008/0071343 A1 | 3/2008 | Mayberry et al. |
| 2008/0077226 A1 | 3/2008 | Ouellette et al. |
| 2008/0077227 A1 | 3/2008 | Ouellette et al. |
| 2008/0082158 A1 | 4/2008 | Tseng et al. |
| 2008/0114441 A1 | 5/2008 | Rust et al. |
| 2008/0132996 A1 | 6/2008 | Drasler et al. |
| 2008/0172122 A1 | 7/2008 | Mayberry et al. |
| 2008/0195191 A1 | 8/2008 | Luo et al. |
| 2008/0262590 A1 | 10/2008 | Murray |
| 2008/0264102 A1 | 10/2008 | Berra |
| 2009/0163951 A1 | 6/2009 | Simmons et al. |
| 2009/0254165 A1 | 10/2009 | Tabor et al. |
| 2010/0030255 A1 | 2/2010 | Berra et al. |
| 2010/0030318 A1 | 2/2010 | Berra |
| 2010/0274340 A1 | 10/2010 | Hartley et al. |
| 2011/0208288 A1 | 8/2011 | Arbefeuille et al. |
| 2011/0218607 A1 | 9/2011 | Arbefeuille et al. |
| 2011/0313503 A1 | 12/2011 | Berra et al. |
| 2012/0123517 A1 | 5/2012 | Ouellette et al. |
| 2012/0143305 A1 | 6/2012 | Berra et al. |
| 2012/0296413 A1 | 11/2012 | Arbefeuille et al. |
| 2013/0274856 A1 | 10/2013 | Arbefeuille et al. |
| 2013/0325099 A1 | 12/2013 | Berra |
| 2013/0331924 A1 | 12/2013 | Ouellette et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi |
| 2014/0277340 A1 | 9/2014 | White et al. |
| 2014/0288627 A1 | 9/2014 | Ouellette et al. |
| 2014/0316510 A1 | 10/2014 | Berra |

FOREIGN PATENT DOCUMENTS

| | | |
|---|---|---|
| DE | 10 2006 053748 B3 | 4/2008 |
| EP | 0 696 447 A2 | 2/1996 |
| EP | 0 873 733 A1 | 10/1998 |
| EP | 0 960 607 A1 | 12/1999 |
| EP | 0 990 426 A1 | 4/2000 |
| EP | 1 177 779 A2 | 2/2002 |
| EP | 1 302 178 A2 | 4/2003 |
| EP | 1 358 903 A2 | 11/2003 |
| EP | 1 369 098 A1 | 12/2003 |
| EP | 1 522 277 A2 | 4/2005 |
| EP | 1 772 120 A2 | 4/2007 |
| EP | 1 923 024 A2 | 5/2008 |
| EP | 1 929 979 A2 | 6/2008 |
| EP | 1 440 673 B1 | 9/2008 |
| EP | 1 982 677 A2 | 10/2008 |
| EP | 1 508 313 B1 | 12/2008 |
| FR | 2 714 816 | 7/1995 |
| FR | 2 722 678 | 1/1996 |
| FR | 2 779 939 A1 | 12/1999 |
| JP | 2008-507331 A | 3/2008 |
| WO | WO 95/23008 | 8/1995 |
| WO | WO 96/09013 A1 | 3/1996 |
| WO | WO 96/23455 | 8/1996 |
| WO | WO 96/31174 | 10/1996 |
| WO | WO 96/38101 | 12/1996 |
| WO | WO 97/33532 | 9/1997 |
| WO | WO 98/20811 | 5/1998 |
| WO | WO 98/23242 | 6/1998 |
| WO | WO 98/42276 A1 | 10/1998 |
| WO | WO 98/53761 | 12/1998 |
| WO | WO 99/25273 | 5/1999 |
| WO | WO 99/37242 | 7/1999 |
| WO | WO 99/65420 | 12/1999 |
| WO | WO 00/02615 | 1/2000 |
| WO | WO 00/30562 | 6/2000 |
| WO | WO 01/17602 A1 | 3/2001 |
| WO | WO 01/21102 A1 | 3/2001 |
| WO | WO 01/24732 A1 | 4/2001 |
| WO | WO 03/015662 A1 | 2/2003 |
| WO | WO 2004/002370 A1 | 1/2004 |
| WO | WO 2004/071352 A1 | 8/2004 |
| WO | WO 2005/023149 A2 | 3/2005 |
| WO | WO 2005/034808 A1 | 4/2005 |
| WO | WO 2005/067819 A1 | 7/2005 |
| WO | WO 2005/081936 A2 | 9/2005 |
| WO | WO 2005/112821 A2 | 12/2005 |
| WO | WO 2006/019551 A1 | 2/2006 |
| WO | WO 2007/008533 A1 | 1/2007 |
| WO | WO 2007/092276 A2 | 8/2007 |
| WO | WO 2007/123956 A2 | 11/2007 |
| WO | WO 2008/031103 A2 | 3/2008 |
| WO | WO 2008/098252 A2 | 8/2008 |
| WO | WO 2009/023221 A1 | 2/2009 |
| WO | WO 2009/124124 A1 | 10/2009 |
| WO | WO 2010/005524 A2 | 1/2010 |
| WO | WO 2010/027485 A1 | 3/2010 |
| WO | WO 2010/105195 A2 | 9/2010 |
| WO | WO 2013/154749 A1 | 10/2013 |

OTHER PUBLICATIONS

Notification Concerning Transmittal of International Preliminary Report on Patentability, International Application No. PCT/US2010/027191, Date of Mailing: Sep. 22, 2011.

\* cited by examiner

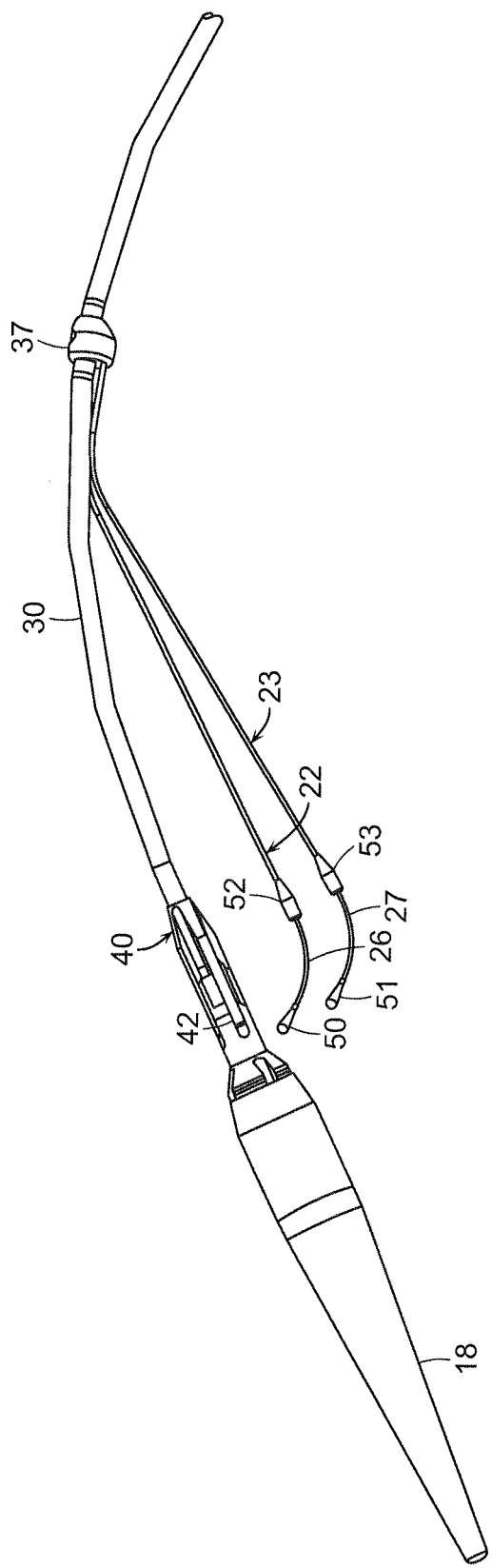

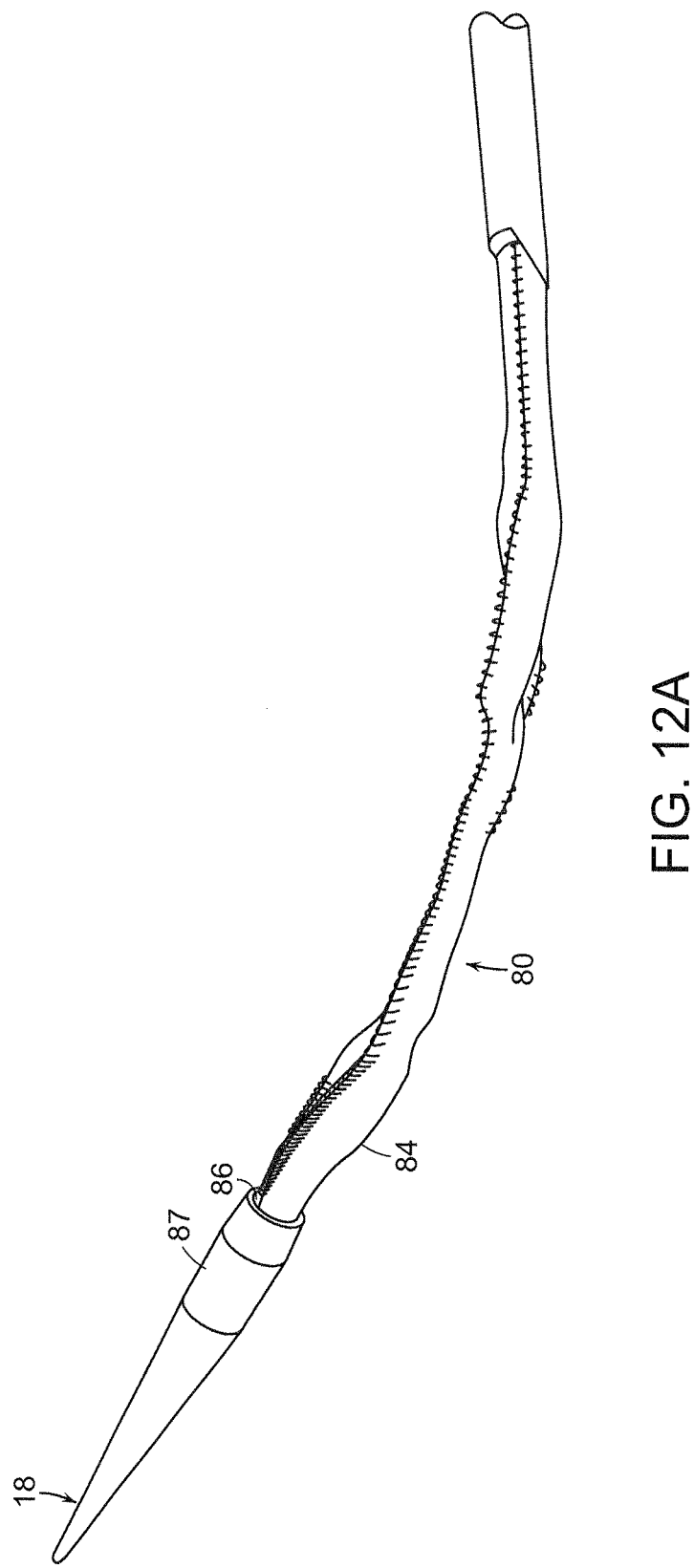

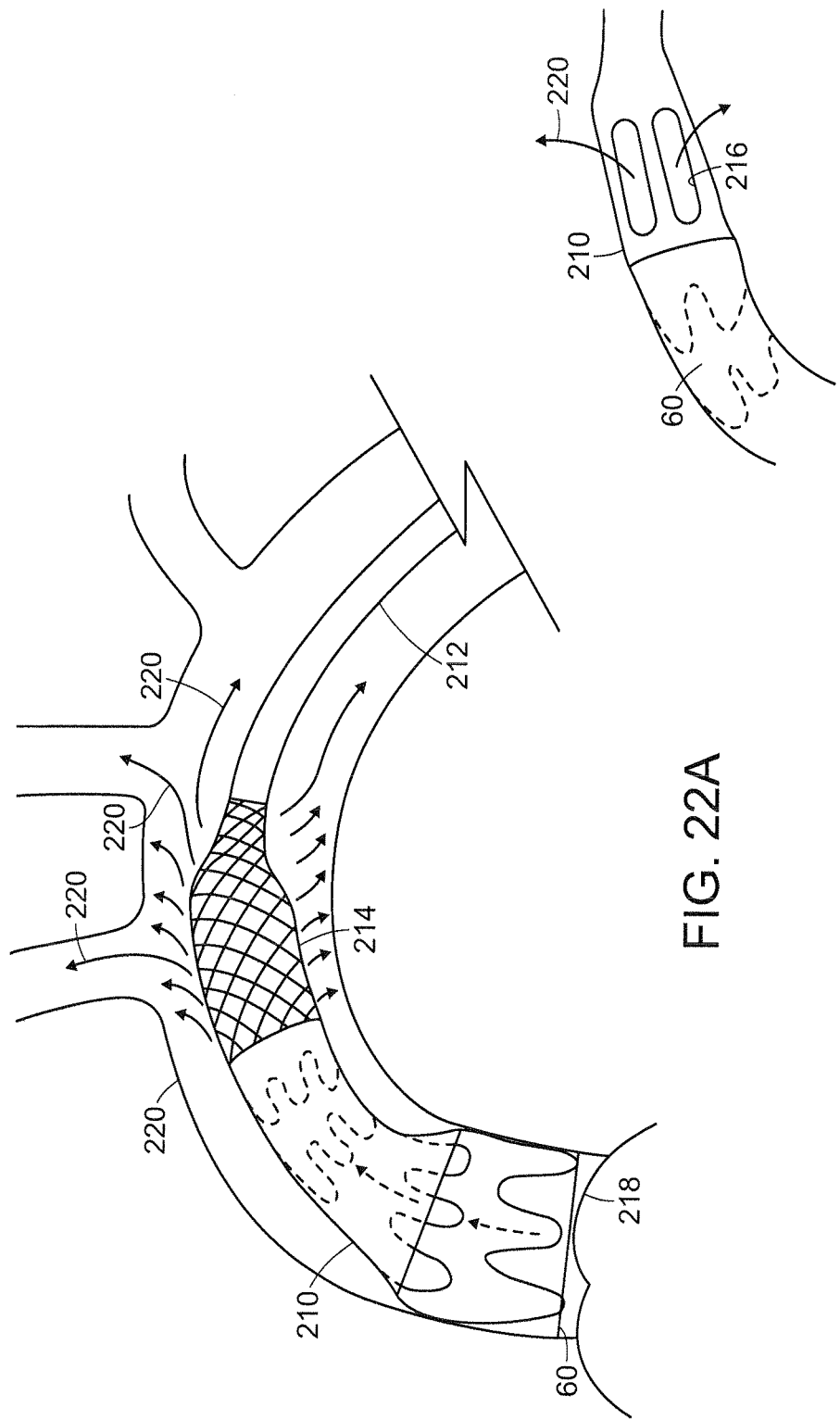

SYSTEM AND METHOD FOR DEPLOYING AN ENDOLUMINAL PROSTHESIS AT A SURGICAL SITE

RELATED APPLICATIONS

This application claims the benefit of U.S. Provisional Application No. 61/160,052, filed on Mar. 13, 2009 and of U.S. Provisional Application No. 61/255,339, filed on Oct. 27, 2009. The teachings of these provisional applications are incorporated herein by reference in their entirety.

BACKGROUND OF THE INVENTION

Endoluminal prostheses for treatment of arterial disease have come into wide use over the past several years. Typically, such prosthesis include a luminal graft material of woven polyethylene terephthalate (PET) supported by self-expanding stents, which are often formed of a shape memory alloy.

Endoluminal stent grafts, so called because they are deployed within a lumen of a blood vessel, are employed to support diseased arterial tissue, such as arterial tissue that has been weakened to thereby form aneurysms, psuedoaneurysms, dissections, penetrating ulcers, and intramural hematomas. Arteries that are most susceptible to these type of disease states, and which would be treatable by implantation of endoluminal stent grafts include, for example, the abdominal aorta, the thoracoabdominal aorta, the descending thoracic aorta, the aortic arch, and the ascending aorta.

Generally, endoluminal prostheses are implanted by femoral access through the femoral artery of a patient. Alternatively, endoluminal devices can be implanted by transapical access through the apex of the heart and the left ventricle to, for example, the ascending aorta and may, when deployed, essentially abut the aortic valve at the sinotubular junction, the region of the ascending aorta between the aortic sinuses (of Valsalva) and where the normal configuration of the aorta is attained.

Implantation of a self-expanding stent graft prosthesis generally requires that it be constrained within a narrow diameter during delivery to the deployment site within the patient. Often, the diameter is constrained by containing the prosthesis within at least one sheath that is capped at a distal end, respective to the surgeon, with a pliable nose cone. The sheath and nose cone are guided through the lumen of the artery by a guidewire that extends axially through and extends from the nose cone of the delivery device within which the prosthesis is contained. Once the nose cone and sheath have been advanced to the surgical site where the prosthesis is to be deployed, the sheath containing the prosthesis can be rotated, if necessary, to properly orient the prosthesis, and then one or more sheaths are retracted to allow the prosthesis to expand, thereby deploying the prosthesis at the intended treatment site.

Several problems can occur by remote deployment of endoluminal prosthesis from a constraining sheath. For example, if the portion of the aorta where the prosthesis is to be deployed has an extreme tortuosity or tight radius of curvature, such as the arch of the aorta, which is arcuate, or because the disease state of the aorta has caused the aorta to have an irregular shape, simple retraction of the sheath, or sheaths, from the prosthesis can cause the proximal end (cranially, with respect to the patient) of the stent graft to fail to properly align with the arterial wall. For example, a portion of the proximal end of the stent graft can rotate backward, toward the surgeon, adjacent to the curve in the vessel thereby causing a failure of the proximal end of the stent graft to form a seal with the artery. This phenomenon is commonly referred to as a "retroflex." Most commonly, rotation of a portion of the proximal end of the stent graft during deployment occurs at an inferior side of a stent graft being deployed within the aortic arch, which has a relatively large diameter. Another problem includes the formation of a "bird's beak," also referred to as a "gap," caused by the stent graft failing to properly conform to an inferior portion curve of the aorta, which most commonly occurs as a result of a deployment sequence that forces the most proximal covered stent of the prosthesis to be deployed last.

Another problem occurs when the stent graft must be deployed close to the junction between the ascending aorta and the aortic valve. Specifically, the nose cone employed to assist guidance of the endoluminal prosthesis to the surgical site restricts the ability of the surgeon to deploy the prosthesis contained in the sheath as close to the ascending aorta at its point of origin.

Therefore, a need exists for a delivery system for implanting a prosthesis and methods of implanting a prosthesis that minimizes or overcomes the above-referenced problems.

SUMMARY OF THE INVENTION

The invention generally is directed to a system and method for implanting a prosthesis and, specifically, for implanting an endoluminal prosthesis at a diseased site of an aorta.

In one embodiment of the invention, the system includes a control lumen, a nose cone fixed at a distal end of the control lumen, and at least one supporting wire fixed at one end, substantially parallel to a major axis of the control lumen and free at an opposite end. The free end of at least one of the supporting wires is arcuate.

In another embodiment, the system of the invention includes a control lumen, a nose cone fixed at a distal end of the control lumen, a stent graft extending about the control lumen, and at least one suture extending from the nose cone to a proximal end of the stent graft and from the stent graft to a fixed location on the control lumen. The suture is releasable from the stent graft by remote activation, whereby retraction of the control lumen releases the suture from the nose cone to thereby deploy the stent graft.

In still another embodiment of the invention, the system includes a control lumen, a nose cone fixed at a distal end of the control lumen, and an inner sheath extending above the control lumen that defines a distal opening at a distal end of the inner sheath. The nose cone is retractable within the inner sheath.

In yet another embodiment of the invention, the invention is a method for implanting a prosthesis that includes delivering a stent graft through an artery to an aneurysm site of a patient, the stent graft being radially constrained by an inner sheath and supported at least in part by a control lumen. The stent graft is also longitudinally constrained by at least one supporting wire extending from a nose cone, from the control lumen or from an outer control tube extending about and slideable along the control lumen, wherein the free end of at least one of the supporting wires is arcuate and extends through a loop hole within a proximal end of the stent graft. The inner sheath is partially retracted from the stent graft, whereby the supporting wire at least partially restricts longitudinal movement of the proximal end of the stent graft until the proximal end of the stent graft is secure within the artery, to thereby prevent rotation of a portion of the proximal end of the stent graft at an inferior portion of the artery. The inner sheath and supporting wire are then retracted, thereby removing the supporting wire from the loop and deploying the stent graft within the artery at the aneurysm site of the patient. The inner sheath and supporting wire can be jointly retracted, thereby removing the supporting wire from the loop and deploying the stent graft within the artery at the aneurysm site of the patient.

In one embodiment, the method further includes the steps of retracting the nose cone within the stent graft after partially retracting the inner sheath. The stent graft is then advanced to a final position within the artery. Thereafter, the inner sheath, nose cone and supporting wires are retracted to fully deploy the stent graft within the artery at the aneurysm site of the patient.

In another embodiment of the invention, the method includes delivering a stent graft through an artery to an aneurysm site of the patient. The stent graft is radially constrained by an inner sheath and supported at least in part by a control lumen, and is further constrained by at least one suture extending from a nose cone at a distal end of the control lumen to a proximal end of the stent graft and extending from the proximal end of the stent graft to a fixed location on the control lumen. This suture is releasable from the nose cone and the stent graft by remote activation. The inner sheath is retracted from the stent graft, whereby the suture at least partially restricts longitudinal movement of the proximal end of the stent graft until the proximal end of the stent graft is secure within an artery, thereby preventing rotation of a portion of the proximal end of the stent graft at an inferior portion of the artery. This suture is then remotely activated, whereby the suture is released from the nose cone and releases the stent graft. The inner sheath is then retracted to thereby deploy the stent graft within the artery at the aneurysm site of the patient.

In still another embodiment, the invention is a method for implanting a prosthesis comprising a control lumen, a nose cone fixed at a distal end of the control lumen, a sheath lumen extending about the control lumen and slideable along the control lumen and an inner sheath extending distally from the sheath lumen and about the control lumen between the nose cone and the sheath lumen, the inner sheath defining at least one through-hole at a proximal end of the inner sheath proximate to the sheath lumen.

In yet another embodiment, the invention is a system for implanting a prosthesis comprising a control lumen, a nose cone fixed at a distal end of the control lumen, an outer control tube extending about the control lumen, an apex clasp at a distal end of the outer control lumen and slideable along the control lumen, a sheath lumen extending about the control lumen, an inner sheath extending distally from the sheath lumen about the outer control tube, the inner sheath including a triangular piece at a distal end of the inner sheath; and a stent graft between the outer control tube and the inner sheath, the stent graft including a proximal end proximate to the nose cone having a clasping stent at the proximal end, wherein the clasping stent has at least one exposed proximal apex releasably held by the apex clasp.

In a further embodiment, the invention is a method for implanting a prosthesis, comprising the steps of delivering a stent graft through an artery to a point distal, relative to the patient, of an aneurysm site of a patient, the stent graft being radially constrained by an inner sheath, and affixed to an outer control tube, and wherein the inner sheath is constrained by an introducer sheath, the stent graft and the inner sheath each including at least one radiopaque marker on superior portions of the stent graft and the inner sheath, the radiopaque markers being separated along a major longitudinal axis of the inner sheath; advancing the inner sheath, the stent graft and the outer control lumen beyond the introducer sheath until the stent graft spans the aneurysm site of the patient; partially retracting the inner sheath from the stent graft, whereby the radiopaque marker of the stent graft overlaps to the radiopaque marker of the inner sheath; positioning a proximal end of the stent graft within the artery; and fully retracting the inner sheath to thereby fully deploy the stent graft within the artery.

This invention has many advantages. For example, the supporting wire of the system for implanting a prosthesis provides longitudinal support for at least a portion of the proximal end of a stent graft, such as a portion of the proximal end of the stent graft that is located an inferior, or inner, portion of a curve, of the aortic arch. This longitudinal restraint limits rotation of a portion of a proximal end of an endoluminal stent at an inferior portion of the aortic arch lumen, thereby causing the proximal end of the stent graft to be properly seated in a plane that is essentially transverse to a major longitudinal axis extending through the aortic lumen at the proximal end of the stent graft. Proper seating of the proximal end of the stent graft prevents seepage of blood beyond and under the prosthesis, thereby increasing the likelihood of successful implant and prolonging useful life of the prosthetic implant. Further, retraction of a nose cone within the stent graft prior to its deployment enables the prosthesis to be deployed within an ascending aorta of a patient essentially within abutting relation with a valve of the heart, thereby providing greater flexibility to the surgeon when placing the stent graft within a patient. In addition, retraction of the nose cone within the stent graft prior to deployment within an abdominal aorta of a patient permits refinements in the placement of the stent graft relative to the aneurysm site in the abdominal aorta, thereby providing greater flexibility to the surgeon when placing the stent graft within the patient. Another advantage of the invention is an inner sheath defining at least one through-hole that permits perfusion or continued flow of blood during deployment of a stent graft.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6 depicts another embodiment of a system of the invention for implanting a prosthesis.

FIG. 12A depicts an embodiment of the invention wherein a nose cone defines a proximal cavity at the proximal end of the nose cone.

FIGS. 15B, 15C and 15E depict fluoroscopic renderings of embodiments of the invention.

FIGS. 22A and 22B depict an embodiment of the invention that includes an inner sheath having at least one through-hole.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principal features of this invention can be employed in various embodiments without departing from the scope of the invention.

The present invention generally is directed to a system and method for implanting an endoluminal prosthesis within a vessel (e.g., artery) of a patient. The system and method employ at least one supporting wire to provide longitudinal support to prevent rotation toward the surgeon of a portion of a proximal end of an endoluminal stent graft during deployment of the stent graft. The proximal end of the stent graft is thereby properly seated at the surgical site proximate to an aneurysm or other diseased portion of an aorta, before complete deployment of the stent graft.

The invention also includes a system that provides for retraction of a nose cone of a delivery system within an endoluminal stent graft prior to complete deployment of the stent graft, thereby permitting abutment of the stent graft to another anatomical feature, such as a heart or arterial valve, during deployment. In still another embodiment, an endoluminal graft delivery system includes a sheath at one end of the endoluminal graft, the sheath being releasable from the endoluminal graft and permitting perfusion distal to the graft.

Figure 1:
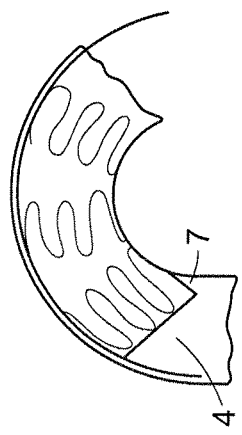
FIG. 1 depicts a prior art system for implanting a stent graft in a lumen of an aorta.
Figure 3:
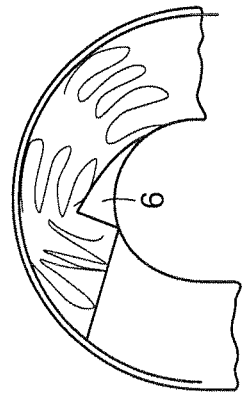
FIG. 3 depicts prior art full deployment of a stent graft with a kink caused by retroflex rotation of the proximal end of the stent graft.
Figure 2:
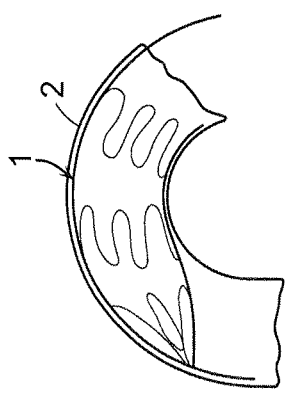
FIG. 2 depicts prior art deployment of a stent graft in a lumen of a curved portion of an aorta from a sheath that permits a proximal end of the stent graft to rotate backward at an inferior portion.
Figure 4:
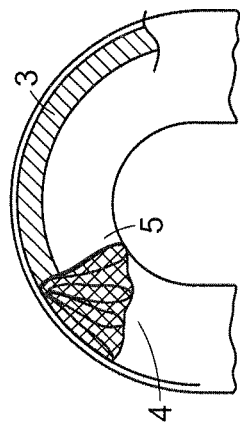
FIG. 4 depicts prior art deployment of a stent graft with a "bird's beak" caused by a sequence of deployment that frees the first proximal covered stent last.

As represented in FIGS. 1-4, deployment of stent graft 1, also referred to herein as an "endoluminal prosthesis" or "prothesis," within the lumen of an aorta 2, particularly a portion of an aorta that exhibits a curvature, such as the arch of the aorta, from the end of a sheath 3, can cause at a proximal end 4 of the prosthesis to rotate backward at an inferior portion 5 of, in a generally longitudinal direction, toward the surgeon, as shown in FIG. 2, thereby causing the fully deployed prosthesis to be folded at the proximal end and creating a kink 6 within the prosthesis, as shown in FIG. 4 or distal buckling of the entire proximal end of the stent graft. FIG. 4 depicts the formation of "bird's beak" 7. The formation of a "bird's beak" can occur with a prosthesis having a bare stent or stent covered with graft material at the proximal end of the prosthesis.

In an embodiment, the invention employs at least one supporting wire as a component of a system for delivering a prosthesis to provide longitudinal support, whereby rotation of the proximal end 4 of the prosthesis during retraction of a constraining sheath is prevented, thereby resulting in deployment of the prosthesis in a fully extended manner, whereby folding back of an inferior portion of a proximal end of the prosthesis and consequent buckling, or crimping, of the prosthesis, as shown in FIGS. 3 and 4, is essentially prevented. Retroflex or such rotation and consequent buckling of the prosthesis can occur in grafts with or without bare stents. A "bird's beak" is particularly prevalent in prostheses that do not have bare stents extending from the proximal (cranial) end of the graft portion of a stent graft. Such stent graft, also known as "non-bare stent grafts," can be employed as prostheses that, when deployed, abut other anatomical structures, such as heart valves. Lack of bare stents at the proximal end of an endoluminal stent graft can make deployment of the stent graft more difficult by providing limited opportunities to control expansion of self-expanding stents of the stent graft as a constraining sheath is retracted during deployment. As a consequence, the inferior portion or the entire portion of a proximal end of an endoluminal stent graft, has a tendency, as described above, to rotate back in a generally longitudinal direction to thereby cause an imperfect seal, possible retroflex or formation of a "bird's beak," as discussed above with respect to FIGS. 3 and 4. The systems and methods of the invention prevent retroflex and the formation of a "bird's beak."

Figure 5A:
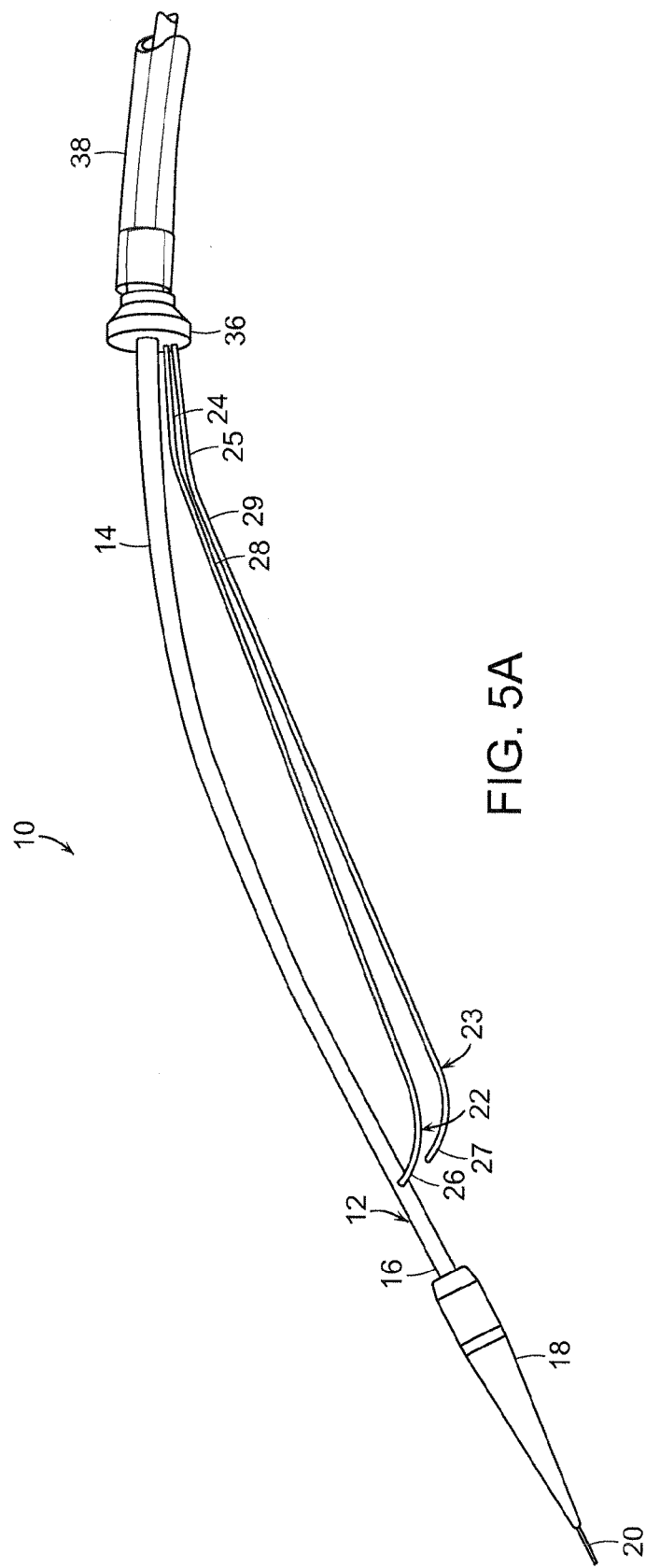
FIG. 5A depicts an embodiment of a system of the invention for implanting a prosthesis.
Figure 5B:
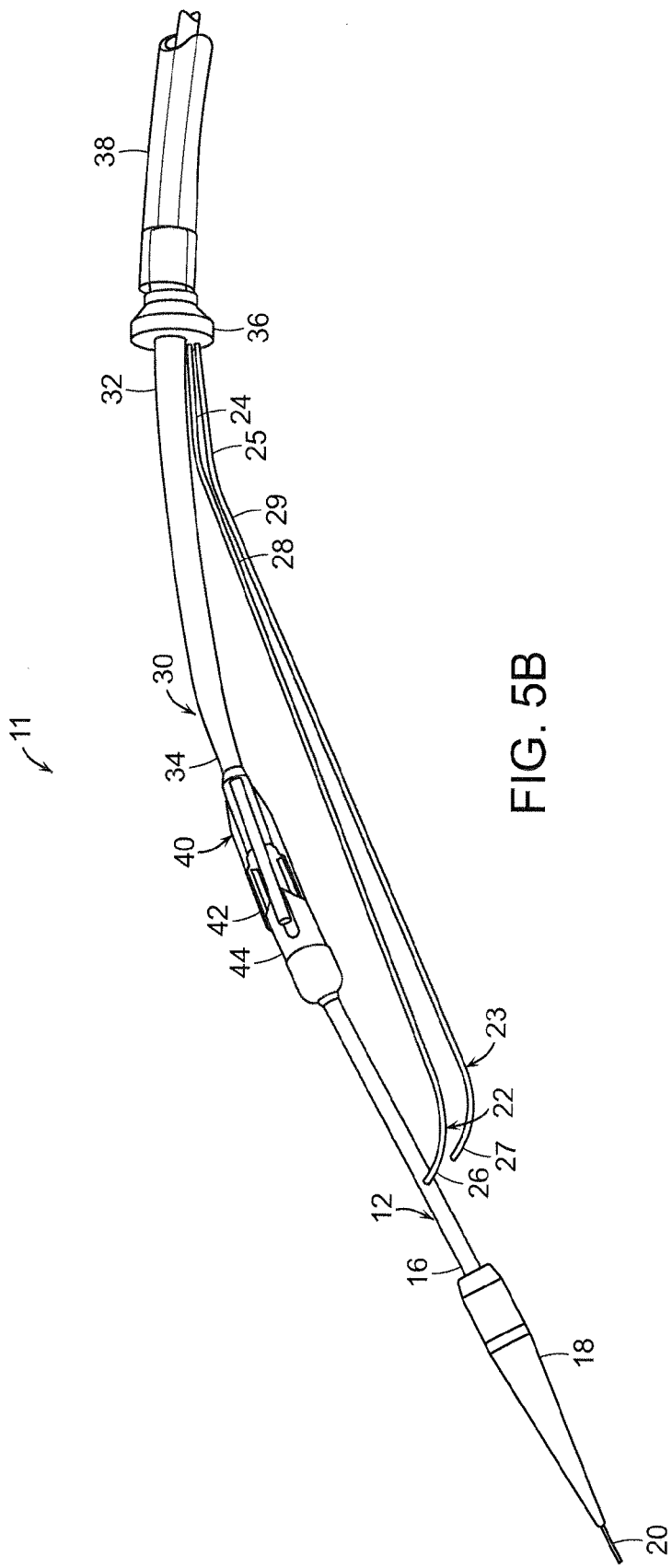
FIGS. 5B and 5C depict embodiments of systems of the invention that include an apex clasp for implanting a prosthesis.
Figure 5C:
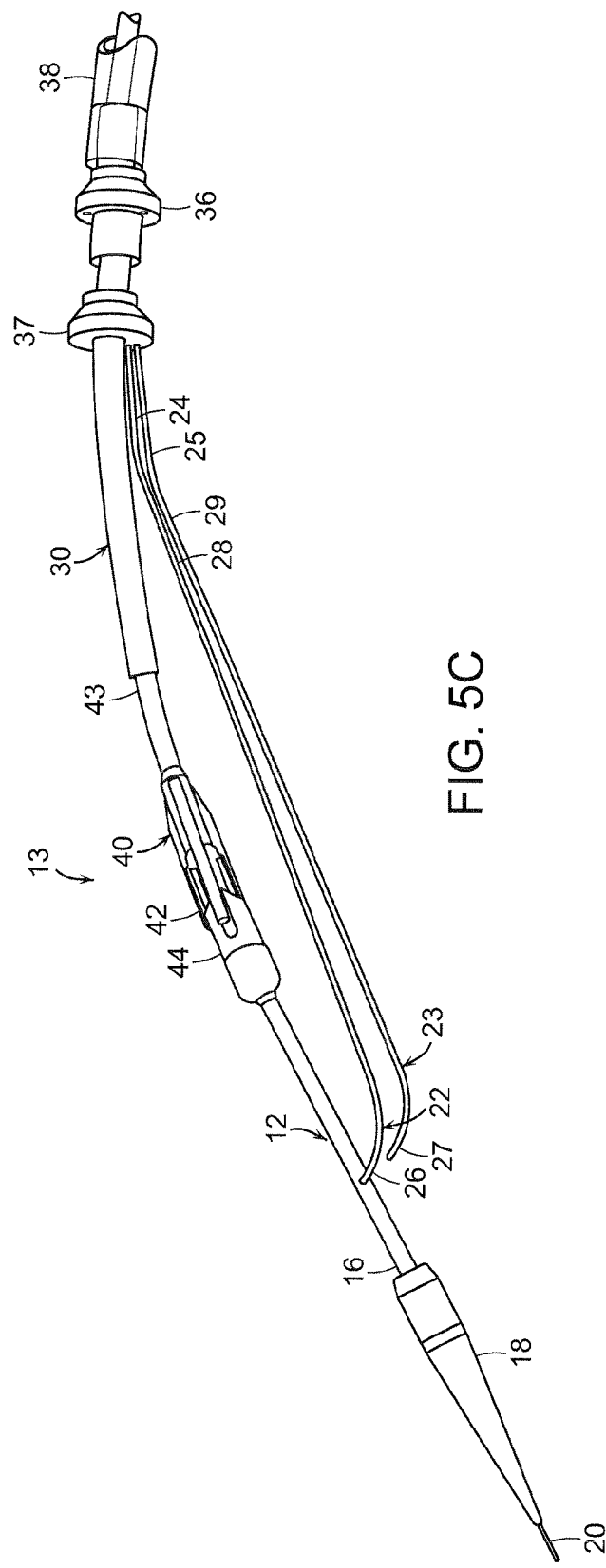

In embodiments of the invention, represented in FIGS. 5A, 5B, 5C, systems 10, 11 and 13, respectively, include, control lumen 12. Control lumen 12 typically is formed of a suitable metal, such as stainless steel, a shape memory metal or a super elastic nickel-titanium alloy, such as a nitinol shape memory alloy; a polymer, such as polyether ether ketone (PEEK); or any combination of a metal, alloy or polymer, in particular, a combination of a metal and an alloy. Control lumen 12 typically is arcuate and defines a lumen extending therethrough having a diameter in a range of between, for example, in a range of about 0.0040 inches (about 0.0030 inches to about 0.0050 inches) ID (inner diameter) and about 0.050 inches (about 0.040 inches to about 0.060 inches) OD (outer diameter). Control lumen 12 includes proximal end 14 and distal end 16.

Nose cone 18 is fixed at distal end 16 of control lumen 12. Nose cone 18 is formed of a suitable material, such as TECO-THANE®, thermoplastic polyurethane elastomer polyether. Control lumen 12 extends through nose cone 18, thereby permitting guidewire 20 to extend through control lumen 12 and from nose cone 18, whereby systems 10, 11, 13 can be advanced along guidewire 20 endoluminally and through an artery (e.g., aorta) of a patient to a surgical site (e.g., ascending aorta, thoracic aorta, descending aorta, abdominal aorta).

Supporting wires 22, 23 are fixed at one end and extend substantially parallel to a major axis of control lumen 12. Supporting wires 22, 23 are free at an end opposite to the fixed end. As shown in FIGS. 5A, 5B and 5C, supporting wires 22, 23 are fixed at proximal ends 24, 25 and are free at distal ends 26, 27. In an embodiment, distal ends 26, 27 of supporting wires 22, 23 are arcuate. Further, supporting wires 22, 23 include cantilever sections 28, 29 that are proximate (near) to proximal ends 24, 25. Typically, supporting wires 22, 23 are formed of a suitable surgical-grade metal, such as stainless steel, or a super-elastic alloy, preferably a nitinol shape memory alloy. The length of supporting wires 22, 23 typically is in a range of about 50 mm to about 75 mm or in a range of about 75 mm to about 100 mm, preferably about 75 mm. The wire diameter at the arcuate end is reduced to ensure that it is easy to straighten and remains very flexible and atraumatic. Supporting wires prevent retroflex during deployment of a stent graft, as depicted in FIG. 4.

Outer control tube 30, shown in FIGS. 5B and 5C, extends about control lumen 12 and is slideable along control lumen 12. Examples of suitable materials of control lumen 12 include PEEK. Typically, outer control tube 30 has an internal diameter in a range of between about 0.050 inches and about 0.060 inches, preferably about 0.055 inches, and an outer diameter in a range of between about 0.070 inches and about 0.075 inches, preferably about 0.071 inches, whereby the thickness of a wall of outer control tube 30, typically, has a range of between about 0.007 inches and about 0.009 inches, preferably about 0.008 inches.

Outer control tube 30 includes proximal end 32 and distal end 34. Buttress 36 is affixed to outer control tube 30, such as at proximal end 32 of outer control tube 30. Supporting wires 22 are fixed at inferior side of buttress 36, thereby causing supporting wires 22 to be clustered. Buttress 36 is formed of a suitable material, such as PEEK, and typically has an outer diameter in a range of between about 0.200 inches and about 0.300 inches, such as about 0.200 inches, about 0.225 inches, about 0.250 inches, about 0.275 inches and about 0.300 inches. Buttress 36 can be sized to fit into the inner diameter of introducer sheath 92. In another embodiment, not shown, at least one supporting wire 22, 23 is fixed directly to control lumen 12, without fixing element 37, and fixing element 37 need not be present.

Pusher support tube 38 extends proximally from buttress 36. In another embodiment, shown in FIG. 5C, wires 22, 23 are fixed to control lumen 12 by fixing element 37 which is separated from buttress 36 and pusher support tube by a length of outer control tube 30. Examples of suitable materials of fixing element 37 include PEEK. Fixing element 37 can be an oblong shape to reduce profile on the opposite side of where the supporting wires are attached.

Apex clasp 40, shown in FIGS. 5B and 5C, is fixed to distal end 34 of outer control tube 30 and is slidable along control lumen 12 with movement of outer control tube 30. Apex clasp 40 includes tines 42 that are in mating relation with receiving section 44 of the apex clasp 40. Typically, tines 42 of apex clasp 40 are formed of a suitable material, such as stainless steel, while receiving section 44 is formed of a suitable material, such as PEEK or stainless steel. Tines 42 are dimensional to receive at least one proximal apex of a clasping stent of a stent graft (FIG. 7E), whereby actuation of apex clasp 40, by retraction of tines 42 from receiving section 44 or nose cone 18 will release the exposed proximal apex of at least one clasping stent during deployment of the stent graft at a surgical site.

Optionally, apex clasp 40 is operable separately from outer control tube 30, whereby outer control tube 30 and supporting wires 22, 23 can be retracted independently of actuation of apex clasp 40, as also shown in FIG. 5C. Separate and independent actuation of apex clasp 40 can be obtained by attachment of apex clasp 40 to tube 43 that extends between outer control tube 30 and control lumen 12.

Figure 7A:
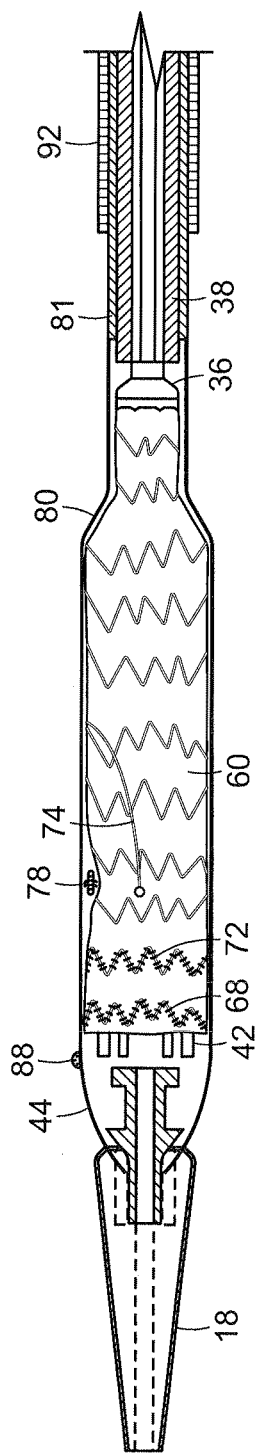
FIGS. 7A, 7B and 7J depict side and longitudinal cross-section views of a portion of embodiments of a system of the invention for implanting a prosthesis.
Figure 7B:
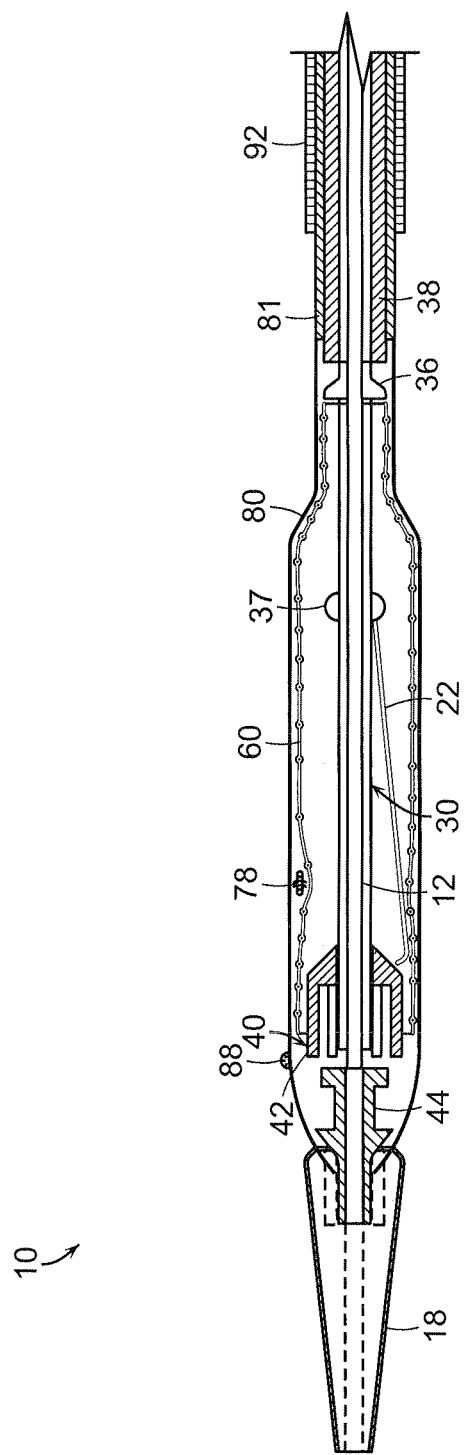
Figure 12B:
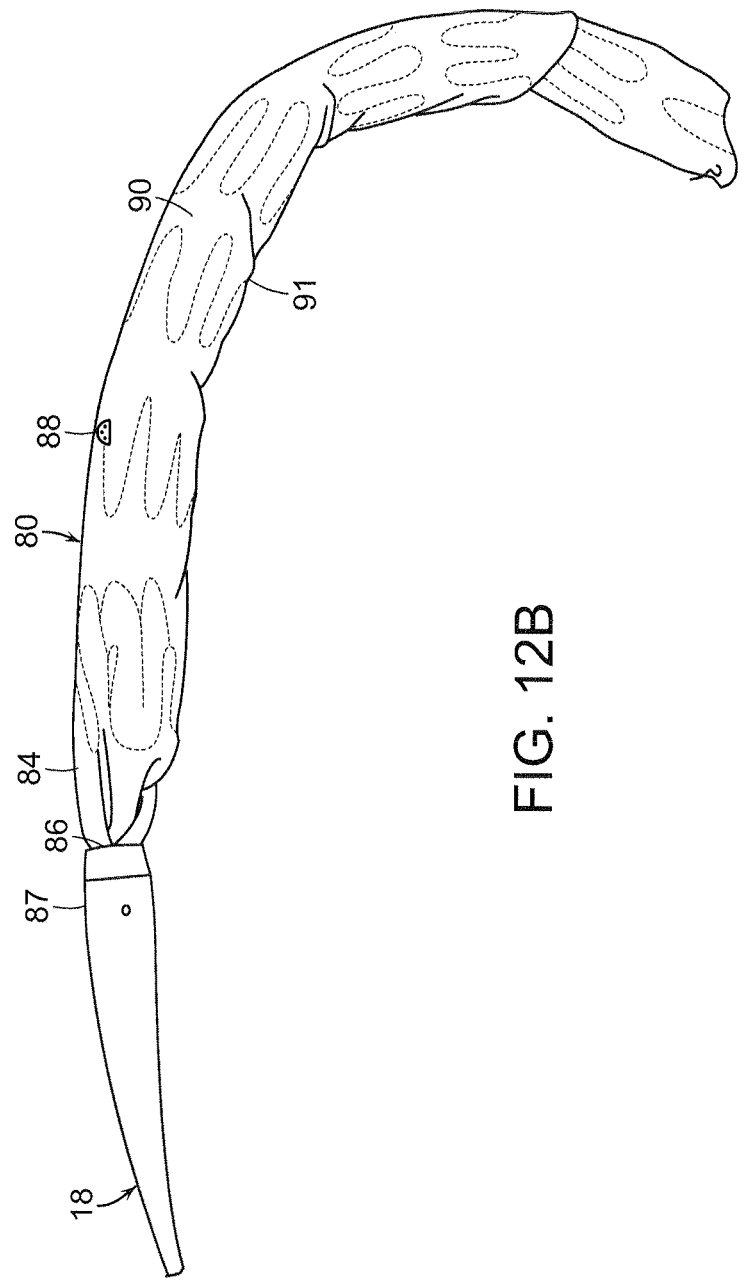
FIG. 12B depicts an embodiment of the invention wherein an inner sheath includes at least one radiopaque marker affixed to a superior portion of the inner sheath.
Figure 12C:
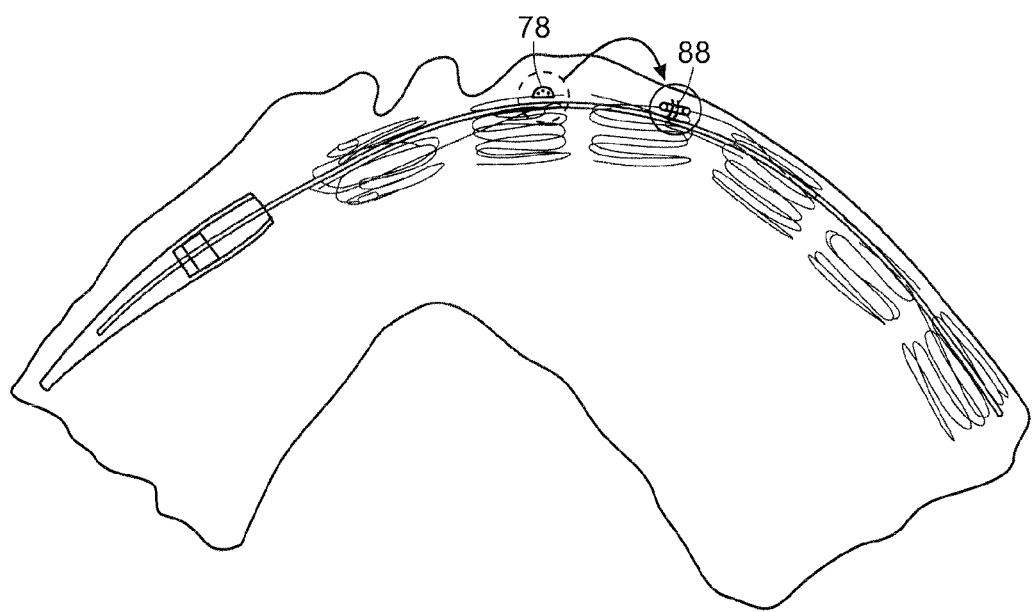
FIG. 12C depicts a fluoroscopic rendering of an embodiment of the methods of the invention whereby partial deployment of a stent graft at a surgical site is indicated by alignment of at least one radiopaque marker of the stent graft and at least one radiopaque marker of an inner sheath.

In an alternative embodiment, represented in FIG. 6, apex clasp 40 is attached to outer control tube 30, fixing element 37 is attached to outer control tube 30 and supporting wires 22, 23 are attached to fixing element 37, whereby apex clasp 40 and supporting wires 22, 23 are jointly retracted by actuation or movement of outer control tube 30. Further, in an alternative embodiment, supporting wires 22, 23 include bulbous tips 50, 51 at distal ends 26, 27, respectively, and stops 52, 53, respectively, having a diameter greater than that of supporting wires 22, 23, proximate to free and distal ends 26, 27 of supporting wires 22, 23. Stent graft 60, shown in FIGS. 7A, 7B and 7J, extends about control lumen 12, supporting wires 22, 23 and outer control tube 30 of system 10. Inner sheath 80 extends about stent graft 60, which, in turn, extends about pusher support tube 38 and is independent and moveable from pusher support tube 38. Sheath lumen 81 typically is formed of PEBAX®, polyether block amine and can include a stainless steel braiding on the interior. Inner sheath 80 extends about stent graft 60, thereby at least partially constraining stent graft 60 prior to deployment at a surgical site. Radiopaque marker 78 is affixed to superior side of stent graft 60 at a distance in a range of about 40 mm and about 60 mm, such as about 40 mm, about 45 mm, about 50 mm, about 55 mm, about 60 mm distal, to proximal end 70 of stent graft 60. Radiopaque marker 88 is fixed to inner sheath 80 by, for example, at least one stitch, and is longitudinally aligned with, but offset from radiopaque marker 78 of stent graft 60. Radiopaque marker 88 can be asymmetric in shape, such as a D-shape, as shown in FIGS. 12B, 12C and 15C.

Figure 7C:
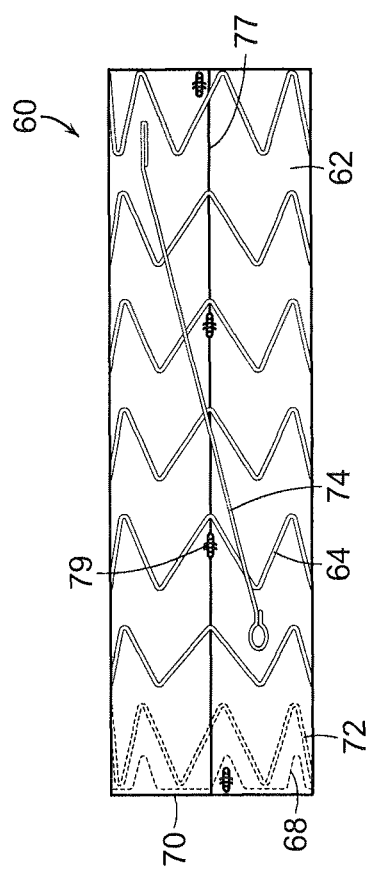
FIGS. 7C and 7K depict embodiments of a stent graft for use in a system of the invention for implanting a prosthesis.
Figure 7D:
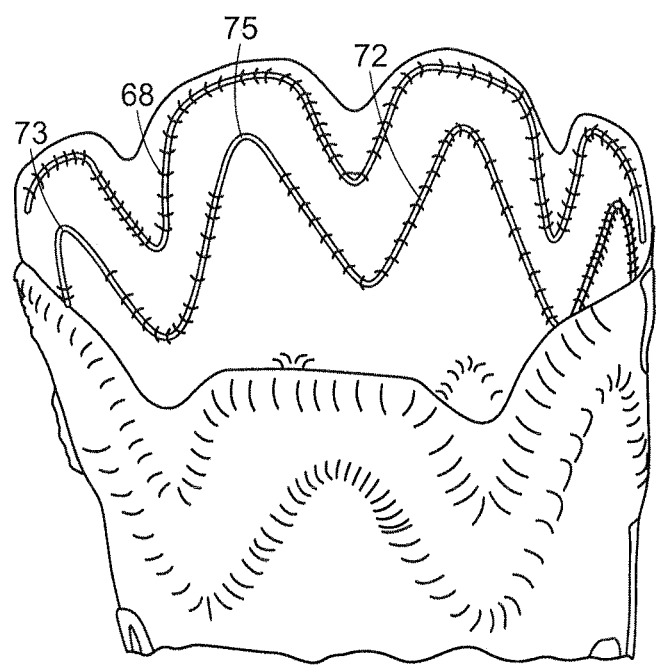
FIG. 7D depicts a crown stent and a clasping stent, with exposed proximal apices, located on the inside of a lumen defined by the graft suitable for use by the invention.
Figure 7E:
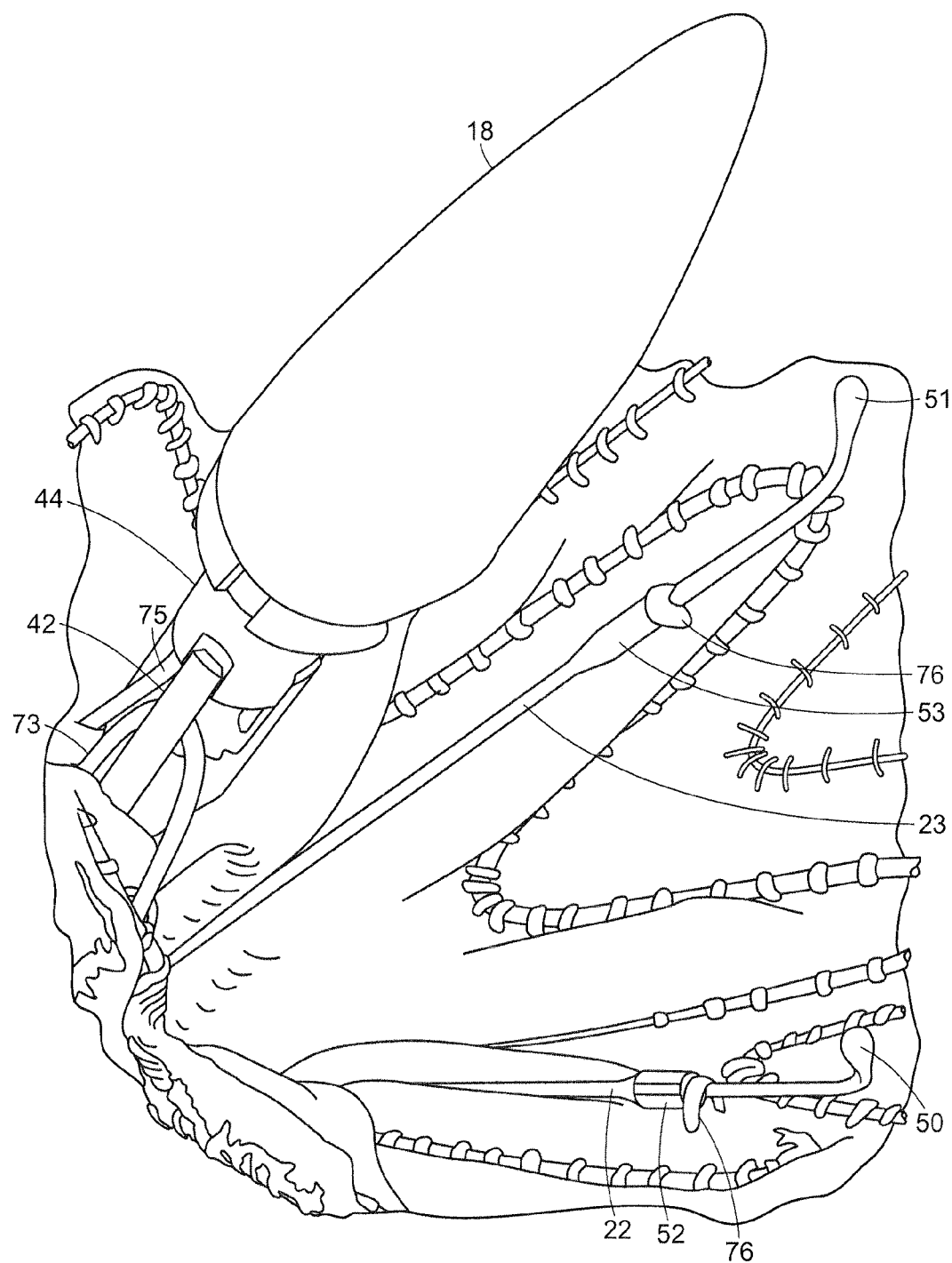
FIG. 7E depicts engagement of the exposed proximal apices of the clasping stent with the tines of an apex clasp of the invention.
Figure 7F:
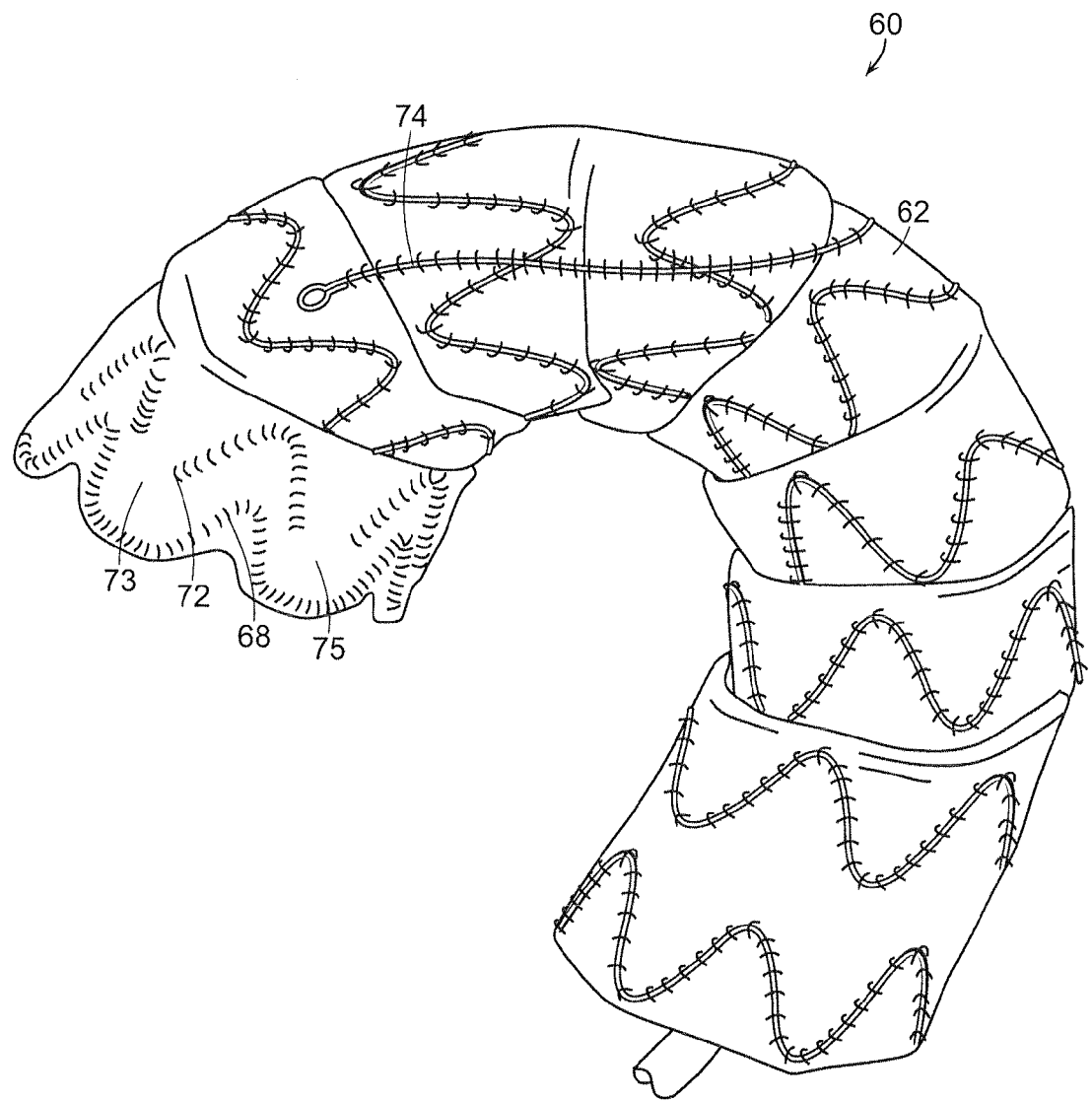
FIG. 7F depicts an embodiment of the stent graft in an arch configuration, as it would be at a surgical site.
Figure 7H:
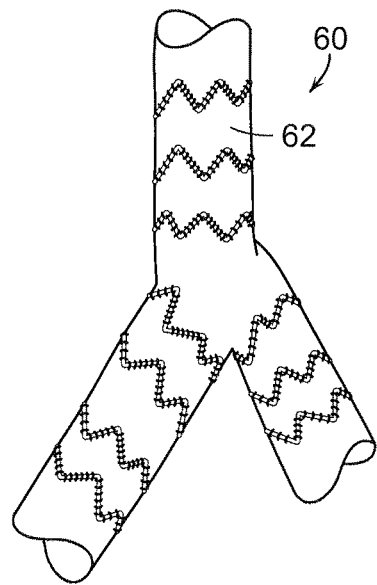
FIGS. 7G, 7H and 7I depict various embodiments of the bifurcated stent grafts suitable for use with the system of the invention for implanting a prostheses.
Figure 7I:
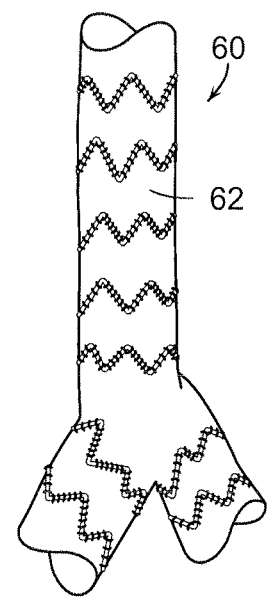
Figure 7G:
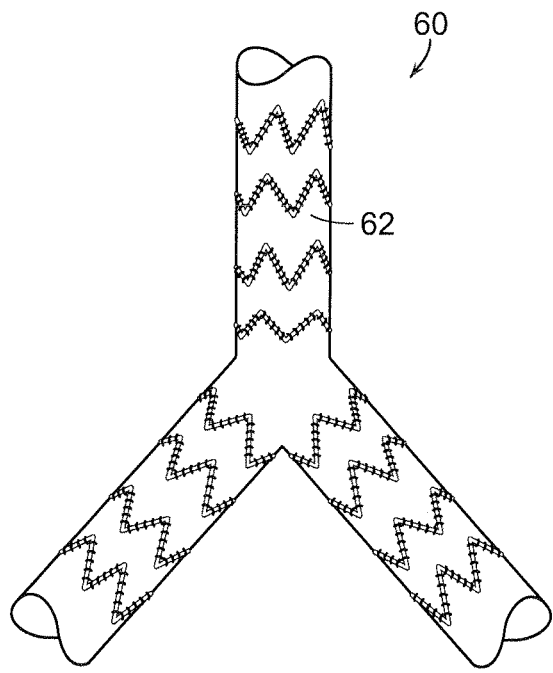
Figure 7J:
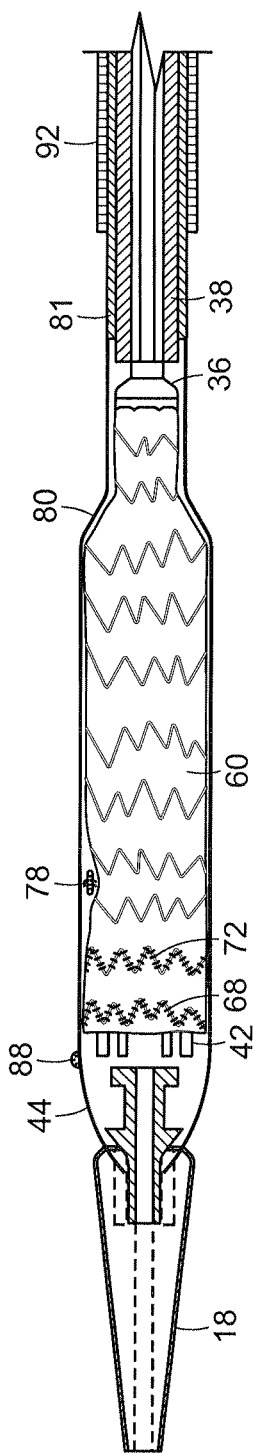
Figure 7K:
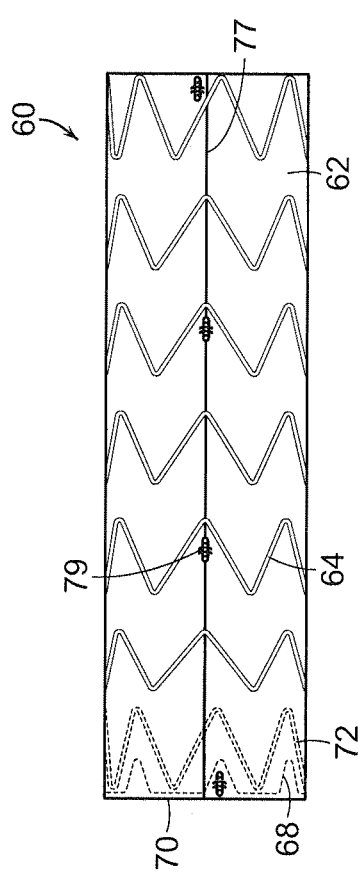

As shown in FIGS. 7C and 7K stent graft 60 includes graft 62 and at least one radiopaque marker 79. In an embodiment, radiopaque marker 79 is a dumb-bell or elongate shape. Examples of suitable materials of graft 62 include PET. Typically, the PET of graft 62 is woven. Alternatively, stent graft 60 can be a bifurcated stent graft having two long legs, and a short and long leg, or two short legs, as shown in FIGS. 7G, 7H, 7I, respectively. Graft 62 is supported by stents 64, which typically are formed of a suitable material, such as a shape memory metal or super elastic nickel titanium alloy, such as nitinol shape memory alloy. Typically, stents 64 are sewn to graft 62 to thereby support graft 62. Stents 64 can be located either within (inside) or outside of a lumen defined by graft 62. Crown stent 68 is inside the lumen of graft 62 and supports proximal end 70 of graft 62. Clasping stent 72, is distal to crown stent 68, relative to the patient. Stent grafts can further include at least one hook or barb, not shown.

As shown in FIG. 7D, clasping stent 72 includes exposed proximal apices 73, 75, which are located within a lumen defined by graft 62. Proximal apices 73, 75, are dimensional for engagement with tines 42 of apex clasp 40, as shown in FIG. 7E. Referring to FIG. 7C, longitudinal support 74 extends along a major axis of stent graft 60 and is affixed to an outside surface of stent graft 60. As shown in FIG. 7F, longitudinal support 74 is on one side of a plane bisecting a major longitudinal axis of stent graft 60, that side being superior to any curve of control lumen 12 when stent graft 60 is secured by systems 10, 11, 13. Likewise, exposed proximal apices 73, 75 are on the side superior to a curve of control lumen 12 and are located proximal to a proximate end of longitudinal support 77. Further, longitudinal support 74 is substantially reverse-mirror symmetrical with respect to the major longitudinal axis of stent graft 60. A second side of stent graft 60 opposite to that which includes longitudinal support 74, is free of longitudinal support. Longitudinal support 74 at superior portion of stent graft 60 can assist in preventing collapse of the superior portion consequent to compliance by stent graft 60 to curvature of an aorta at a surgical site at an aneurysm, where stent graft 60 is to be deployed.

Typically, longitudinal support 74 is curved. Referring back to FIG. 7C, longitudinal support 74 has centerline 77 that is parallel to the longitudinal axis of stent graft 60. Longitudinal support 74, when curved, can be curved with respect to the centerline 77 in a manner that is about a mirror image of a portion of longitudinal support 74 on either side of a longitudinal plane of centerline 77, which is referred to herein as "reverse-mirror symmetrical."

In an embodiment, stent graft 60 can include longitudinal support 74 affixed, such as sewn, to the outside of graft 62, as shown in FIG. 7C. In another embodiment shown in FIG. 7K the longitudinal support is not present on graft 62.

Figure 8:
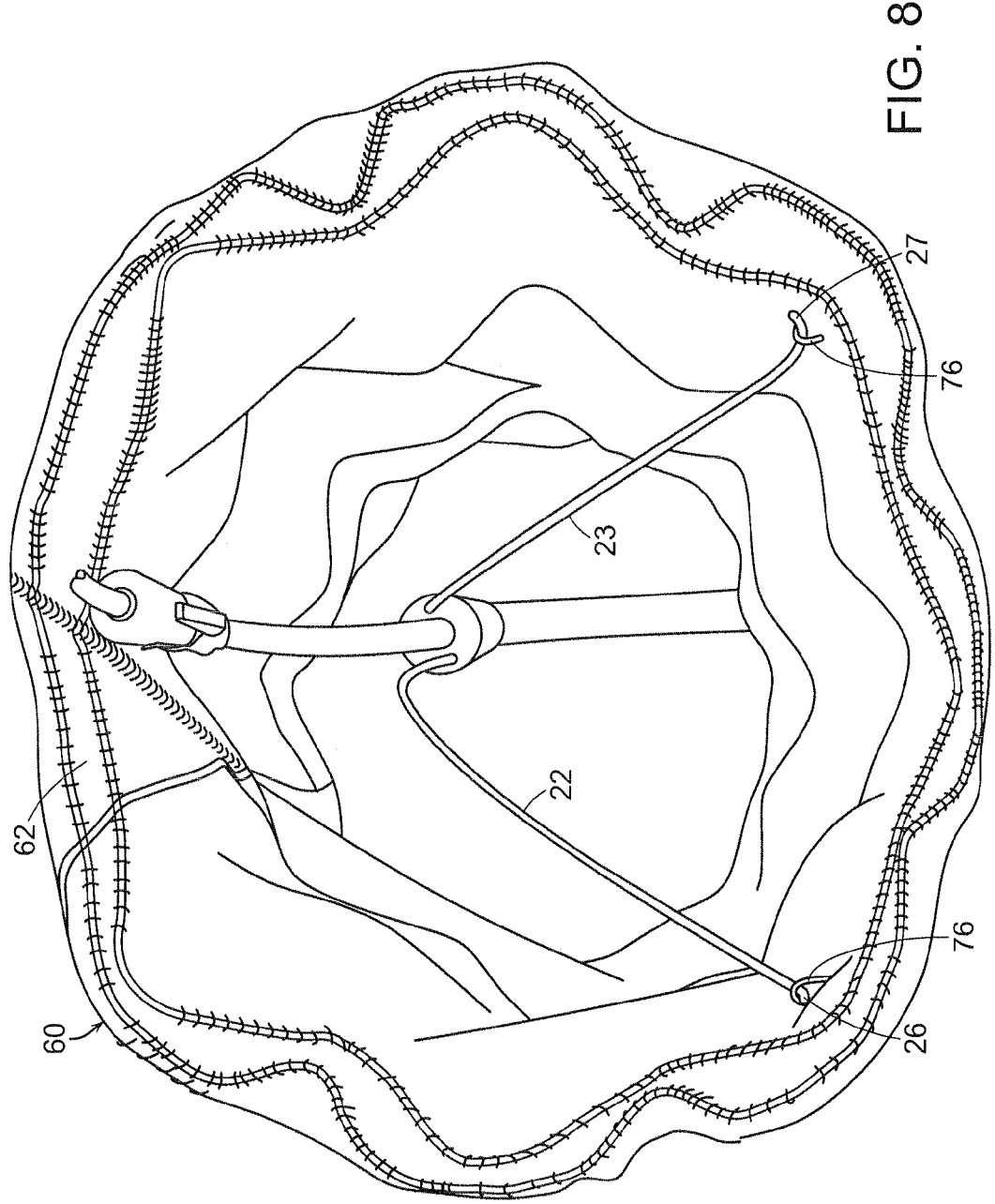
FIG. 8 depicts suture loops on an inside surface of the stent graft.

As shown in FIG. 8, stent graft 60 includes at least one suture loop 76 on an inside surface of graft 62. Distal ends 26, 27 of supporting wires 22, 23 extend through suture loops 76, whereby supporting wires 22, 23 can be released from suture loops 76 by proximal retraction of supporting wires 22, 23 toward the surgeon. Referring back to FIG. 7E, exposed proximal apices 73, 75 are secured to systems 11, 13 by tines 42 of apex clasp 40.

Figure 9A:
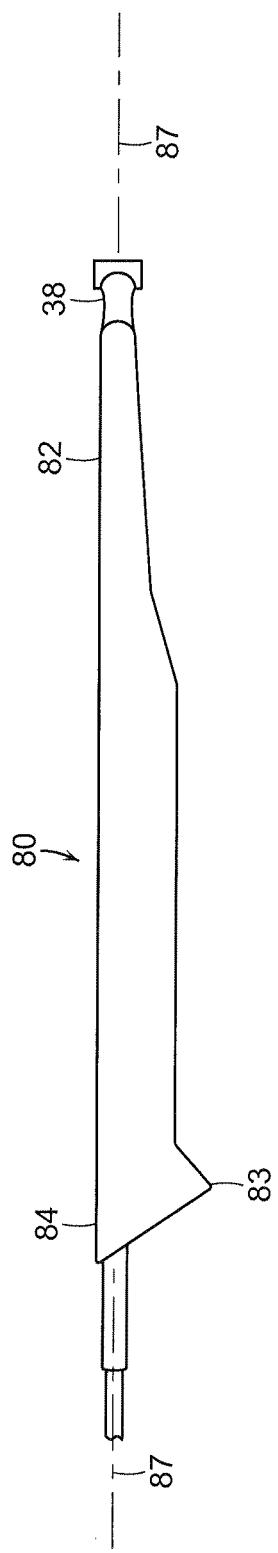
FIGS. 9A and 9B depict embodiments of an inner sheath in a system of the invention for implanting a prosthesis.
Figure 9B:
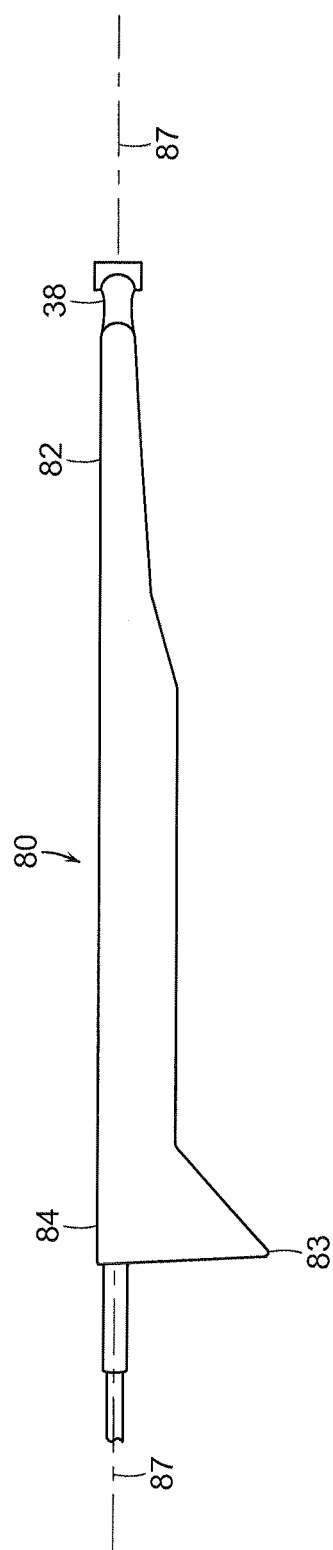
Figure 10:
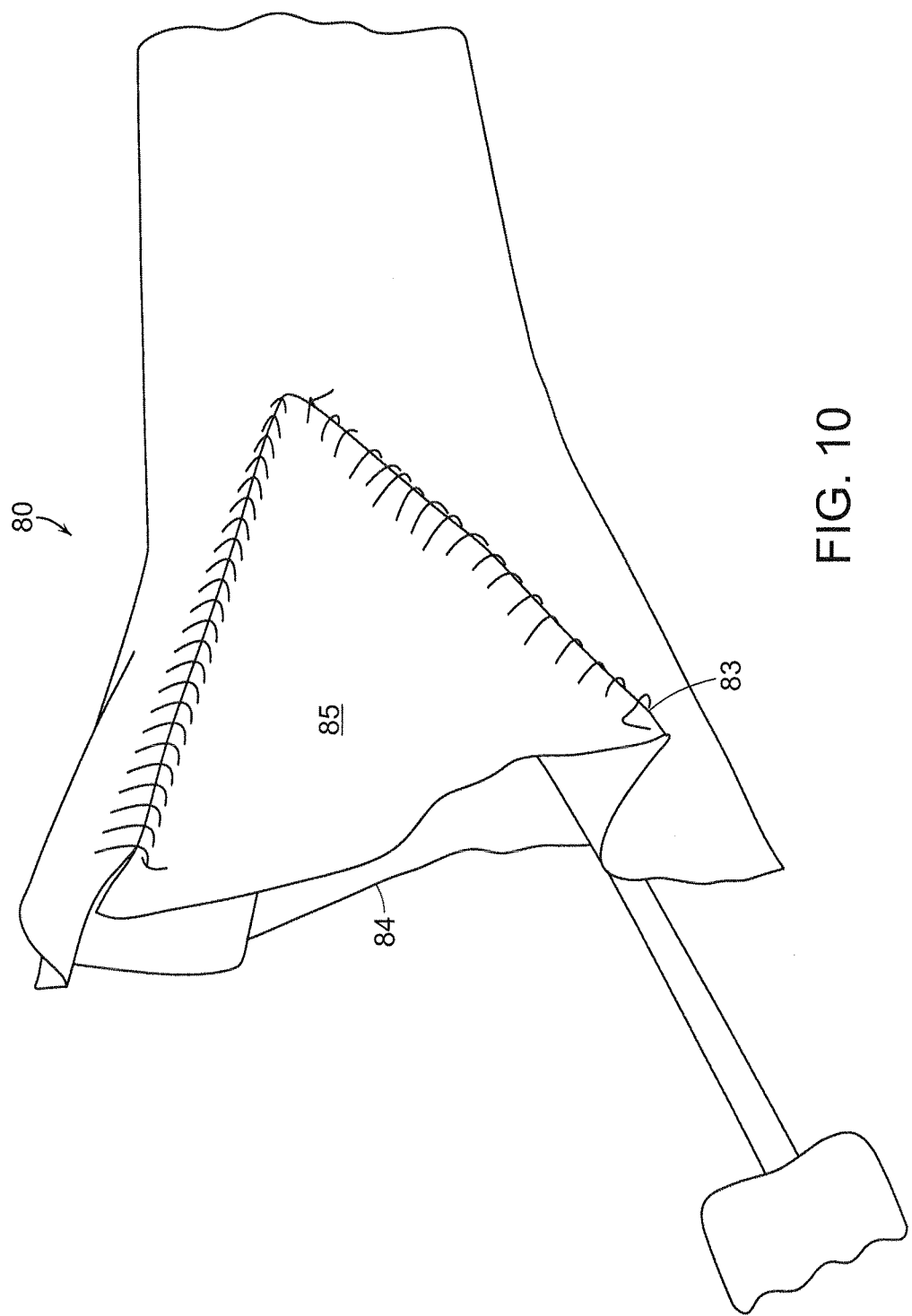
FIG. 10 depicts an alternative embodiment of a distal end of an inner sheath in a system of the invention for implanting a prosthesis.
Figure 11A:
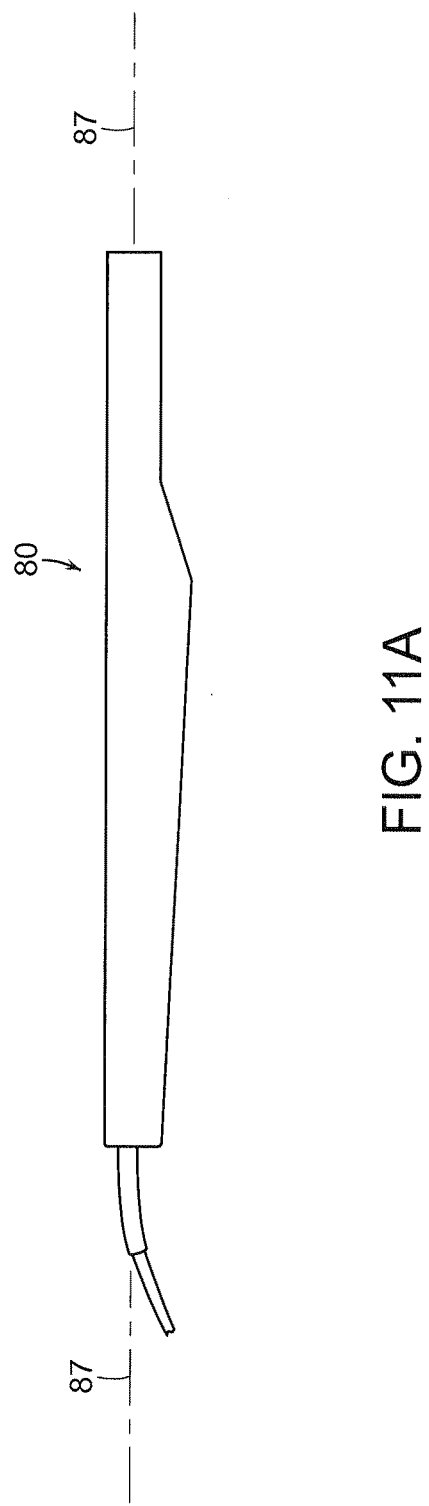
FIGS. 11A and 11B depict other alternative embodiments of an inner sheath in a system of the invention for implanting a prosthesis.
Figure 11B:
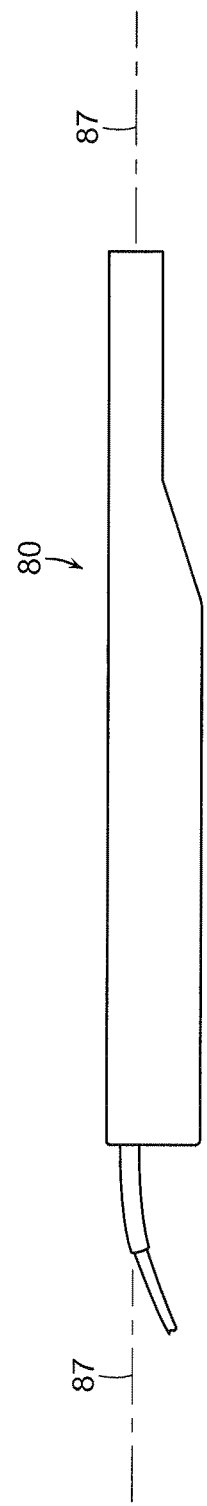

As can be seen in FIGS. 9A and 9B, inner sheath 80 is tapered between proximal end 82 and distal end 84, whereby the diameter of a lumen defined by inner sheath 80 is greater at distal end 84 than at proximal end 82. Further, inner sheath 80 is flared downwardly at inferior portion 83 of distal end 84. Further, the flared opening is asymmetric. Inferior portion 83 can be tapered distally as shown in FIG. 9A or straight relative to the most proximal end of inner sheath 84 as shown in FIG. 9B. As shown in FIG. 10, triangular piece 85 of inner sheath 80 is attached at inferior portion 83 of distal end 84. In an alternative embodiment, shown in FIGS. 11A and 11B, inner sheath 80 defines a distal opening that is not flared or is not asymmetric. Inner sheath 80 includes major longitudinal axis 87.

In another embodiment of the invention, shown in FIG. 12A, nose cone 18 defines proximal cavity 86 at a proximal end 87 of nose cone 18. Distal end 84 of inner sheath 80 can fit within proximal cavity 86, whereby retraction of inner sheath 80 from nose cone 18 releases distal end 84 of inner sheath 80 from proximal cavity 86.

Referring to FIG. 12B, radiopaque marker 88 is affixed to superior portion 90 of inner sheath 80. Inner sheath 80 has inferior portion 91. Sufficient partial deployment of stent graft 60 to finalize positioning of proximal end 70 of stent graft 60 at a surgical site will be indicated by alignment and, preferably, superimposing of radiopaque markers 78 and 88, as shown in FIG. 12C.

Figure 13:
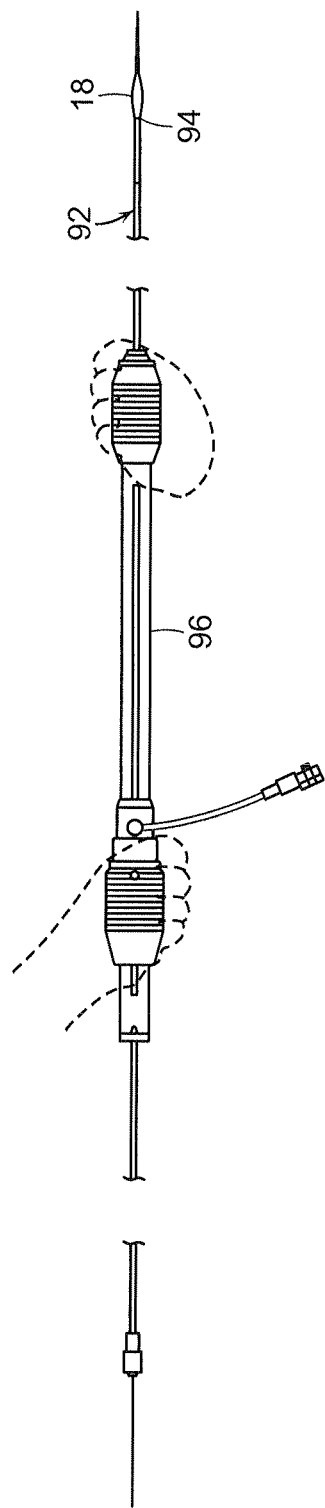
FIG. 13 depicts an embodiment of a system of the invention for implanting a prosthesis where an inner sheath containing a stent graft is constrained prior to delivery by a introducer sheath.

The inner sheath containing the stent graft, is constrained prior to delivery by introducer sheath 92, shown in FIG. 13. Nose cone 18 when fully retracted, forms an interference fit with distal end 94 of introducer sheath 92, thereby sealing the stent graft and inner sheath within introducer sheath 92 for delivery to a patient and within the patient to the surgical site where the stent graft is to be deployed. Introducer sheath 92 is, in turn, affixed to handle 96 of system 10, 11, 13, 100.

Figure 14A:
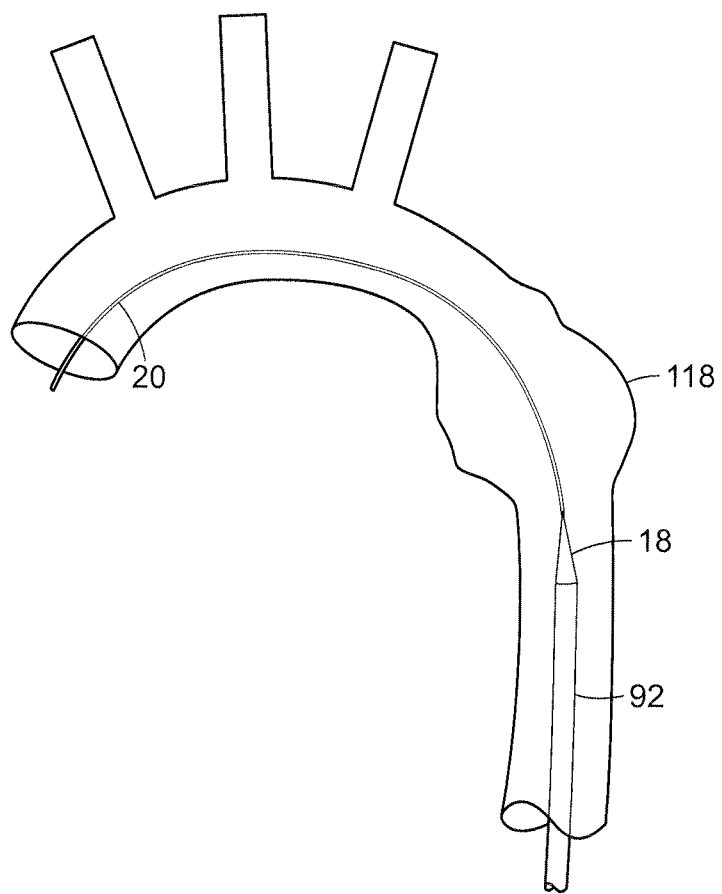
FIGS. 14A-14E depict an embodiment of the invention during implantation of a prosthesis at an aneurysm site.
Figure 14B:
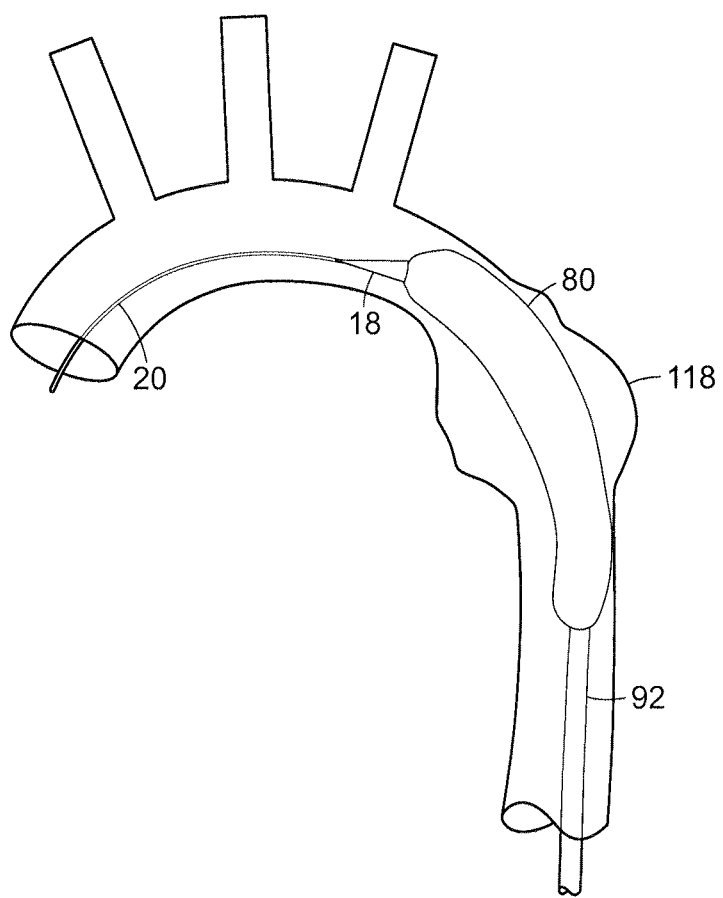
Figure 14C:
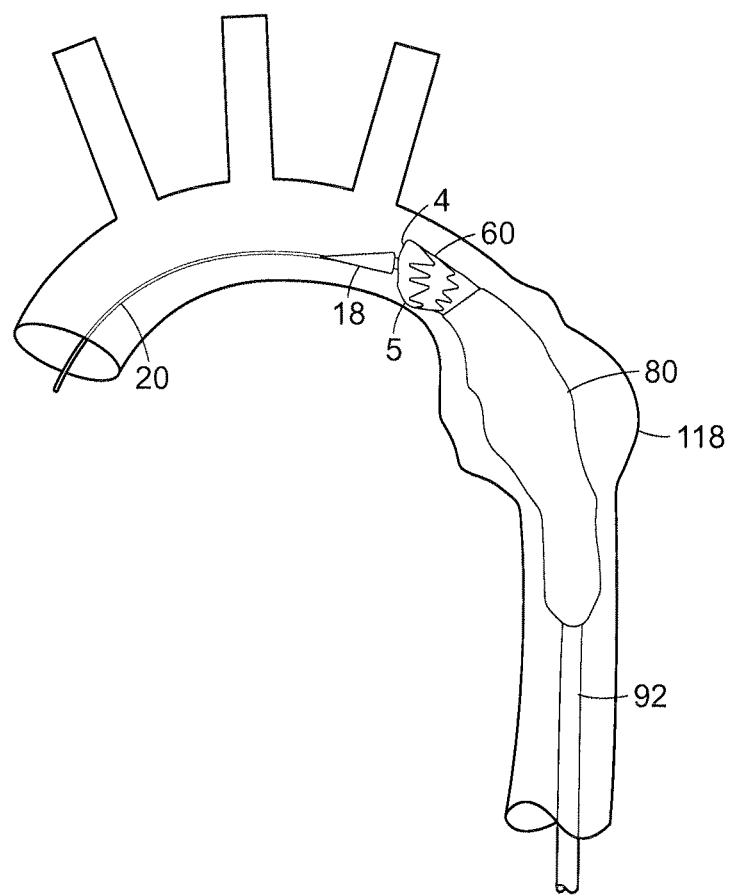
Figure 14D:
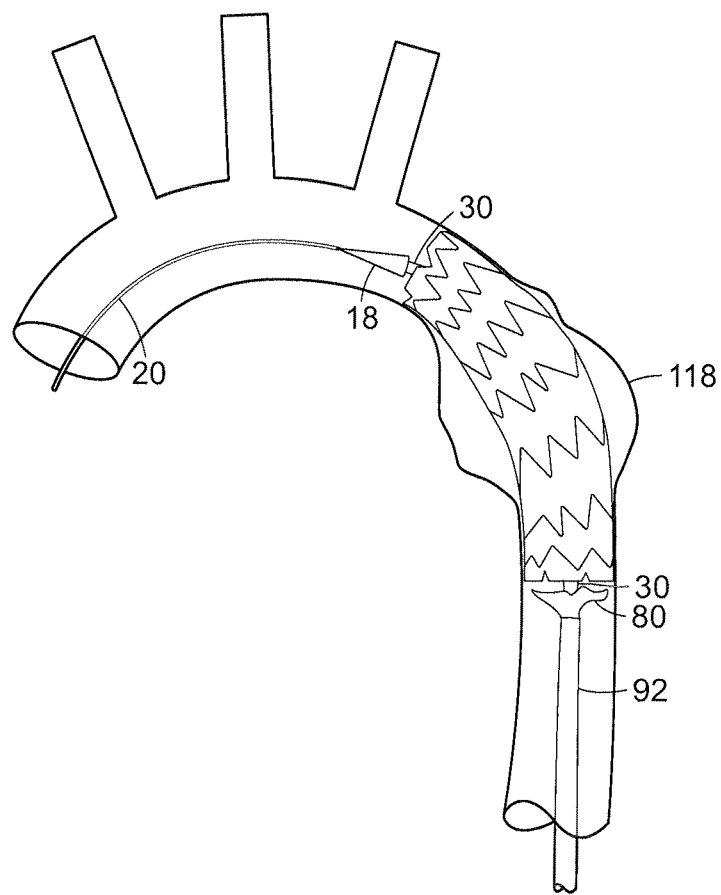
Figure 14E:
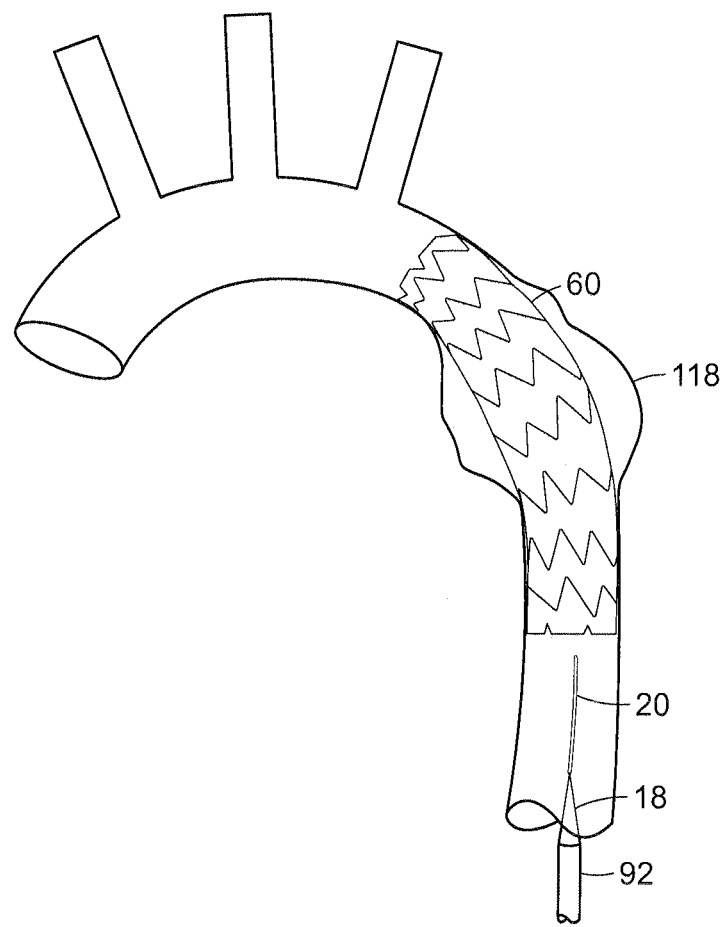

A method of the invention includes advancing introducer sheath 92, while nose cone 18 is fully retracted, and in interfering relation with introducer sheath 92, endoluminally within an artery of a patient until nose cone 18 is proximate to a surgical site of a patient. Control lumen 12, outer control tube 30, pusher support tube 38, apex clasp 40, and sheath lumen 81 (FIG. 5, et seq.), are all independently moveable from handle 96 (FIG. 13). The surgical site can be, for example, an aneurysm site 118 of, for example, an abdominal aorta, ascending aorta, a thoracic aorta or a descending aorta. As shown in FIGS. 14A-14E advancement of system 10, 11, 13 through an artery of a patient typically occurs by first introducing a guidewire through the aorta from a femoral artery of the patient (transfemoral access) to beyond the intended deployment site. Guidewire 20 extends through control lumen 12 of system 10, 11, 13. System 10, 11, 13 is then advanced along the guidewire until nose cone 18 and introducer sheath 92 are proximal, relative to the surgeon, of the surgical site, as shown in FIG. 14A. Nose cone 18, control lumen 12, pusher tube support 38, stent graft 60 and inner sheath 80 (FIG. 5, et seq.) are then all advanced beyond introducer sheath 92, until nose cone 18 and proximal end 70 of stent graft 60 are distal to the aneurysm, relative to the surgeon, as shown in FIG. 14B, at which point stent graft 60 and inner sheath 80 will no longer be constrained by introducer sheath 92. Instead, stent graft 60 will be constrained within inner sheath 80, which has a larger internal diameter than that of introducer sheath 92 once inner sheath 80 and stent graft 60 have been advanced beyond introducer sheath 92. Inner sheath 80 is then retracted relative to the remainder of system 10, 11, 13 as shown in FIG. 14C, wherein supporting wires 22, 23 (not shown) prevent rotation of inferior portion 5 of proximal end 4 of stent graft 60, also known as "retroflex." Supporting wires 22, 23 are then withdrawn by the merger, along with activation of apex clasp 40, if present, to release stent graft 60. Inner sheath 80 is then fully retracted to fully deploy stent graft 60, as shown in FIG. 14D. System 10, 11, 13 is then withdrawn through deploying stent graft 60, as shown in FIG. 14E. The same general method can be employed to deploy similar stent grafts at surgical sites other than the thoracic aorta or aortic arch, including, for example, the descending aorta or ascending aorta; or bifurcated stent grafts at the abdominal aorta.

Figure 15A:
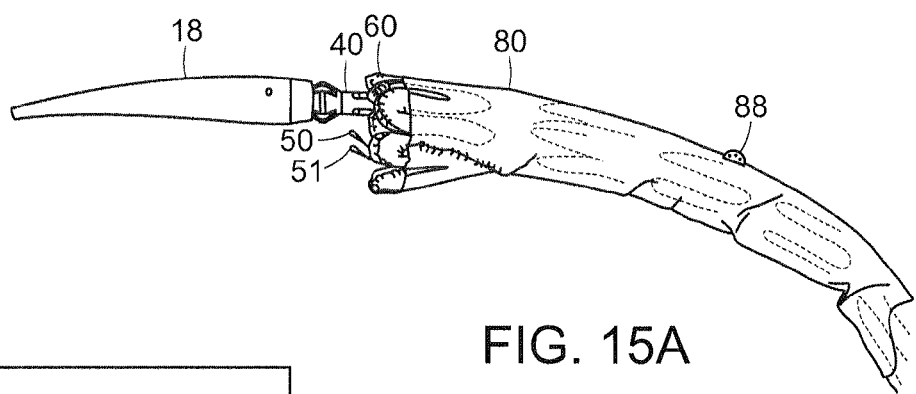
FIGS. 15A-15E depict different views of an embodiment of the invention during deployment of a prosthesis.
Figure 15B:
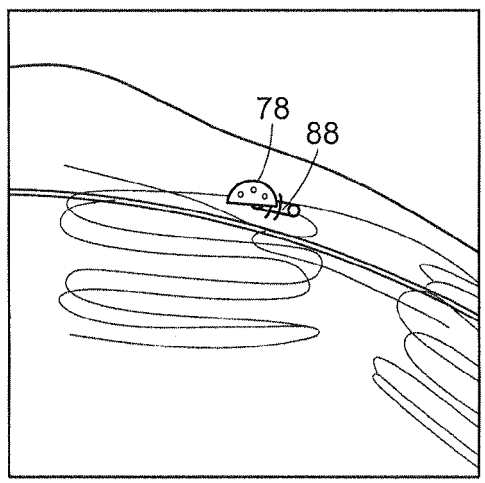
Figure 15C:
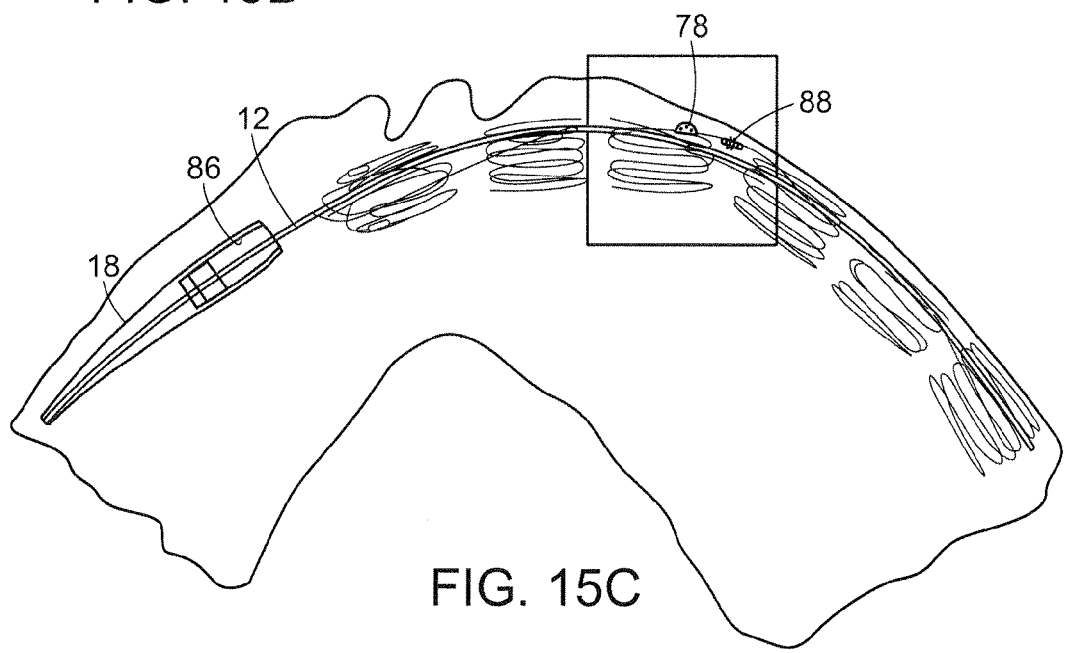
Figure 15D:
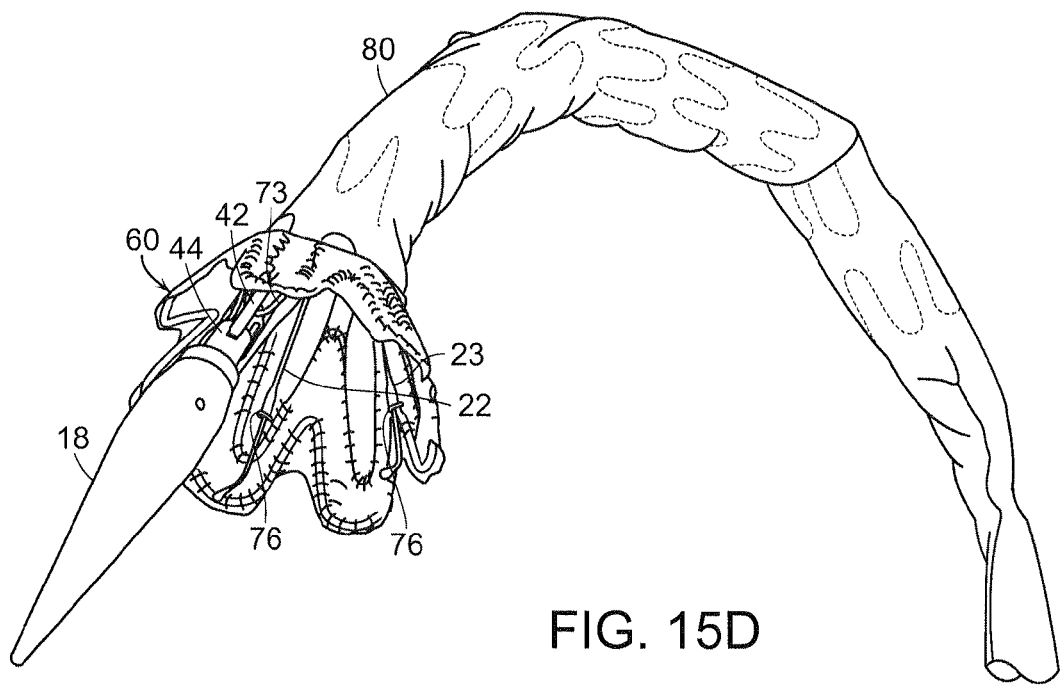
Figure 15E:
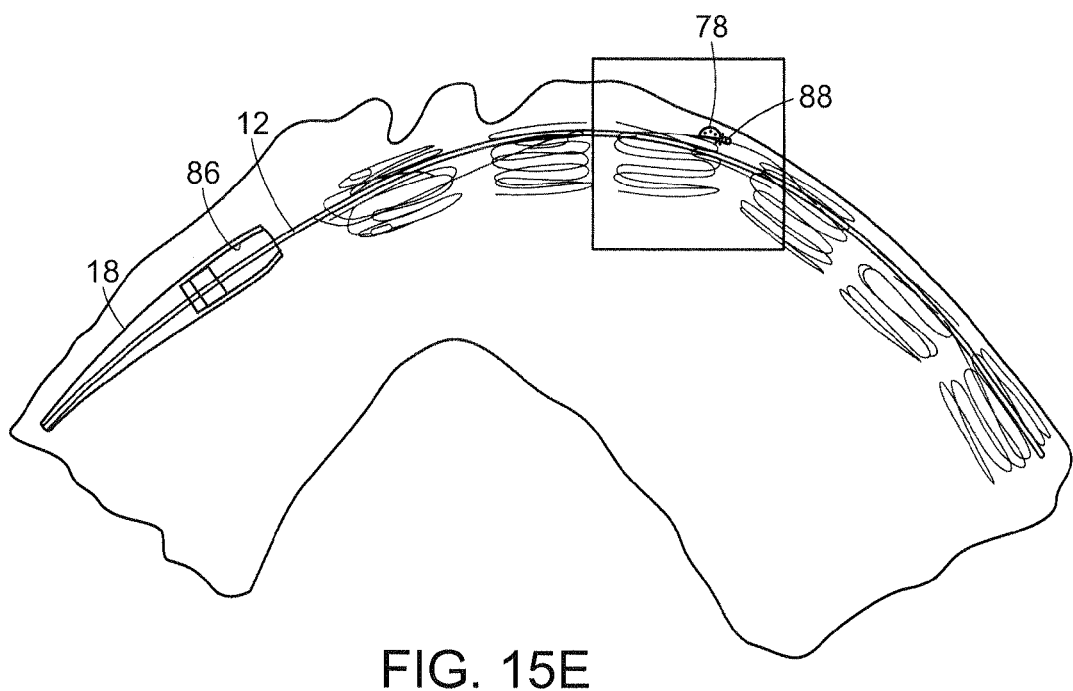

More specifically, as can be seen in FIG. 15A, inner sheath 80 is then partially retracted relative to control lumen 12 and the pusher support tube to thereby expose proximal end 70 of stent graft 60. Preferably, inner sheath 80 is retracted by retraction of sheath lumen 81 until the radiopaque marker 78 on stent graft 60 shifts from a position of non-alignment with radiopaque marker 88, as shown in FIG. 15C, to a position of alignment with radiopaque marker 88, as shown in FIG. 15E, a detail of which is shown in FIG. 15B. Upon this partial deployment of stent graft 60, supporting wires 22 prevent rotation of an inferior portion 5 of proximal end 70 of stent graft 60 in a generally longitudinal direction parallel to that of a major axis of control lumen 12 at proximal end 70 by providing resistance to that rotation through longitudinal restraint imposed by supporting wires 22 on suture loops 76 of stent graft 60.

In an embodiment, the stent graft and the inner sheath each include a radiopaque marker longitudinally aligned along a path of relative movement of the inner sheath and stent graft during deployment of the stent graft, and spaced apart from each other, whereby the partial retraction of the inner sheath will cause overlap of the radiopaque markers. The radiopaque markers are on superior portions of the inner sheath and the stent graft. In an embodiment, the radiopaque marker in the inner sheath is asymmetric, such as is D-shaped, wherein a straight portion of the D-shaped marker is aligned with a major longitudinal axis of the inner sheath. In an embodiment, the radiopaque marker of the stent graft is elongate and substantially aligned with the major longitudinal axis of the inner sheath.

Stent graft 60 can then be rotated about its major longitudinal axis or otherwise positioned by the surgeon by handle 96 (FIG. 13). Once proximal end 70 is properly positioned by the surgeon, apex clasp 40, if present, can be remotely activated by the surgeon to release exposed proximal apices 66 within stent graft 60 (FIG. 15D). Control lumen 12, pusher support tube 38 and sheath lumen 81 can then be retracted, separately or jointly (FIGS. 5A through 5E). Retraction of pusher support tube 38 will withdraw supporting wires 22 from suture loops 76. Continued retraction of control lumen 12, pusher support tube 38 and sheath lumen 81 will fully deploy stent graft 60 at the surgical site. System 10 can then be removed from the patient. The formation of a "bird's beak" is prevented by systems and methods of the invention. The apex clasp only partially clasps an inner stent, such as exposed proximal apices 73, 75 of clasping stent 72, and the proximal end of stent graft 60 is initially deployed, then fully deployed as the inner sheath is retracted to thereby prevent formation of a "bird's beak."

In an alternative embodiment, system 11 or 13 lack supporting wires 22, 23, and fixing element 37. In this embodiment, a similar method described above would be employed to deploy stent graft 60, with the exception that supporting wires would not be present. At least one exposed proximal apex 73, 75 of clasping stent 72 would be engaged with tines 42 of apex clasp. In this embodiment, inner sheath 80 includes triangle piece 85, shown in FIG. 10. Further, this embodiment would be most suitable for implantation of stent graft 60 into a vessel, such as a blood vessel (e.g., an artery) having an internal diameter of equal to or less than about 27 mm (e.g., about 20 mm, about 22 mm, about 24 mm, about 26 mm, and 27 mm). Stent graft 60 in this embodiment typically would have an expanded external diameter in a range of between about 22 mm and about 30 mm (e.g., about 25 mm).

Figure 16:
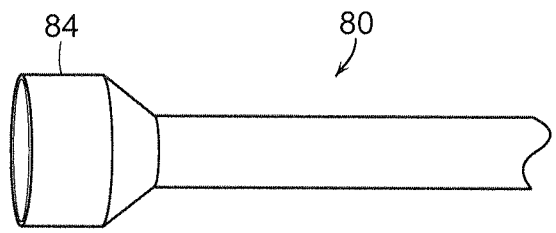
FIG. 16 depicts an embodiment of the inner sheath in the system of the invention.
Figure 17:
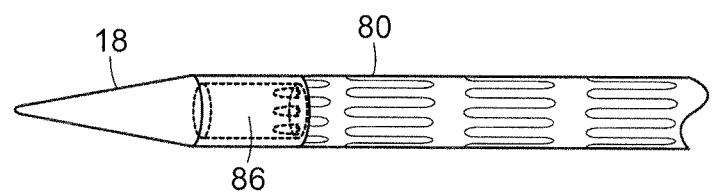
FIGS. 17 and 18 depict yet another embodiment of the invention for implanting a prosthesis.
Figure 18:
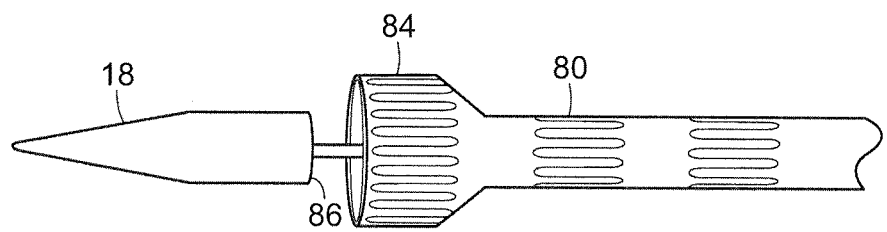
Figure 19A:
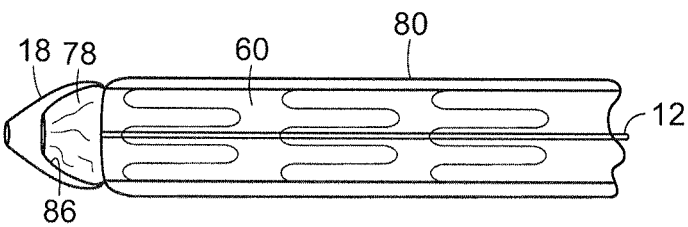
FIGS. 19A-19D depict still another embodiment of the invention for implanting a prosthesis.
Figure 19B:
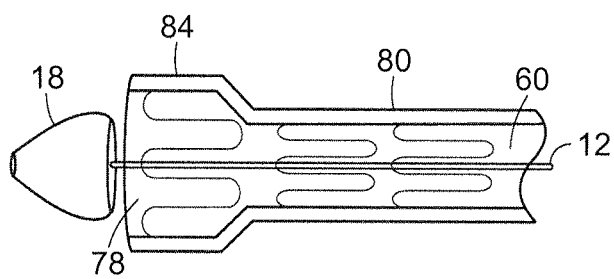
Figure 19C:
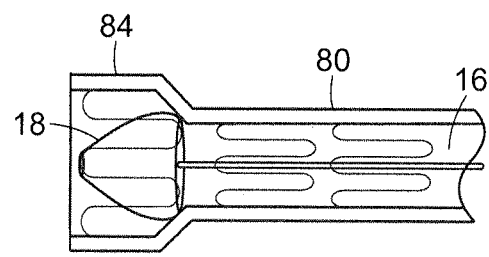
Figure 19D:
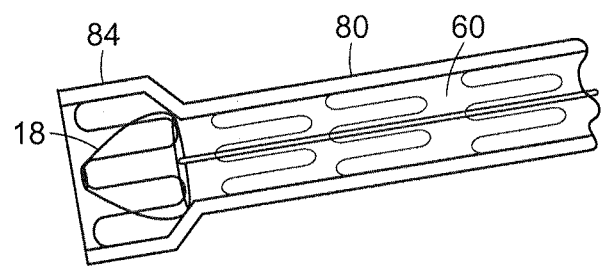

In an alternative embodiment, shown in FIG. 16 wherein inner sheath 80 includes distal end 84 having a greater diameter than the remainder of inner sheath 80. Nose cone 18 defines proximal cavity 86, as can be seen in FIG. 17 following advancement of nose cone 18, stent graft 60 and inner sheath 80 beyond introducer sheath 92, inner sheath 80 is retracted by retracting sheath lumen 81 sufficient to release distal end 84 of inner sheath 80 from proximal cavity 86 of nose cone 18, as shown in FIG. 18. Proximal end 70 of stent graft 60 thereby expands to a constrained diameter equal to that of the internal diameter of distal end 84 of inner sheath 80. In one embodiment, not shown, radiopaque markers 78 and 88 overlap upon release of proximal end 70 of stent graft 60 from proximal cavity 86 of nose cone 18. Alternatively, inner sheath 80 includes second radiopaque marker 98, which overlaps radiopaque marker 78 of stent graft 60 upon release of proximal end 82 of inner sheath 80 from proximal cavity 86. In this embodiment, radiopaque marker 98 would be distal to radiopaque marker 88, and radiopaque markers 78 and 88 would overlap when sheath 80 is partially retracted from stent graft 60. The surgeon can then orient proximal end 70 of stent graft 60 prior to partial or complete deployment of stent graft 60. Where complete deployment follows, the presence of supporting wires 22 is optional.

Alternatively, following the release of distal end 84 of inner sheath 80 from proximal cavity 86, nose cone 18 is retracted within stent graft 60 by retraction of control lumen, as shown in FIGS. 19A through 19D. The surgeon can then further advance stent graft 60 and inner sheath, either without, or jointly with, nose cone 18, until proximal end 78 of stent graft 60 is properly positioned at the surgical site, such as by abutment or near abutment with an anatomical feature, such as a heart valve (e.g., aortic valve). Thereafter, sheath lumen 81 and inner sheath 80 can be retracted, either with or without retraction of nose cone 18, to at least partially deploy stent graft 60. In one embodiment, not shown, supporting wires 22 restrain an inferior portion of proximal ends 70 from rotating back toward the remainder of stent graft 60 in a direction generally longitudinal to a major axis of stent graft 60. Upon final positioning of proximal end 70, apices 66 are released from tines 42 of apex clasp 40 by remote retraction of tines 42 at handle 96, and system 11, 13 is retracted to fully deploy stent graft 60 at the surgical site. Alternatively, system 11, 13 is retracted to fully deploy stent graft 60 without use of supporting wires 22 or apex clasp 40.

Figure 20A:
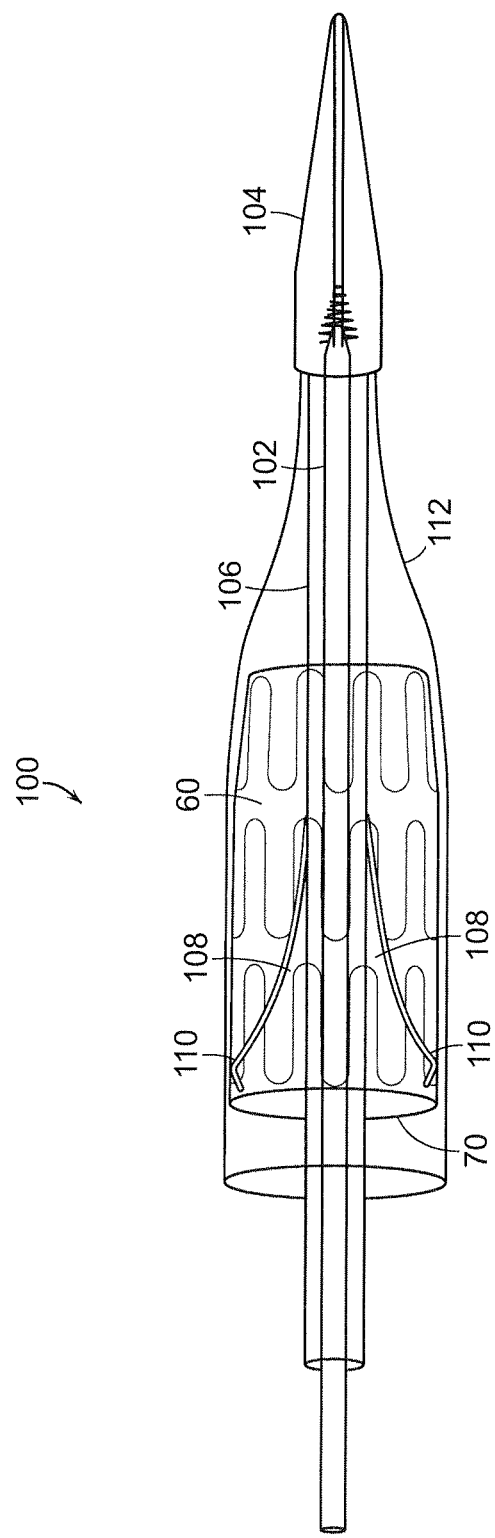
FIGS. 20A and 20B depict embodiments of the invention, for implanting a prosthesis by entry through the left ventricle of a patient's heart.
Figure 20B:
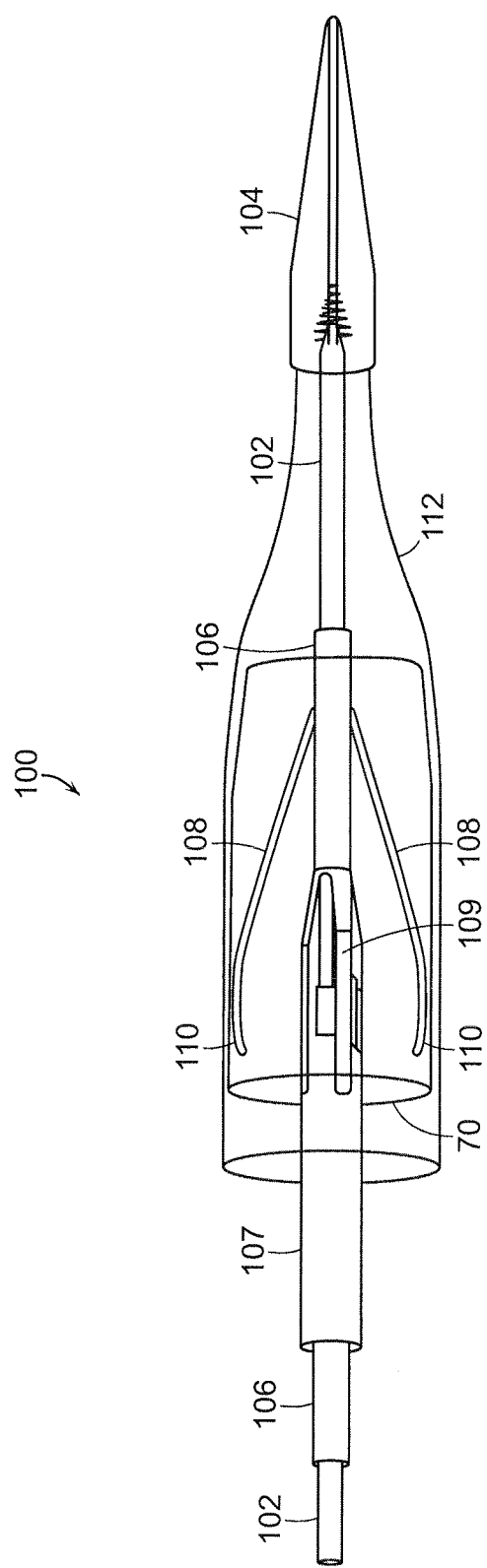

In other embodiments, shown in FIGS. 20A and 20B, system 100 includes control lumen 102 to which is affixed nose cone 104. Outer control tube 106 extends about control lumen 102 but is not connected to nose cone 104. At least one supporting wire 108 is fixed to outer control tube 106. Supporting wire 108 extend substantially parallel to a major axis of control lumen 102 and are free at an end opposite to where it is fixed to outer control tube 106. Typically, free end 110 of supporting wire 108 is arcuate. Stent graft 60 is disposed about outer control tube 106 and about supporting wires 108. Inner sheath 112 is fixed to nose cone 104 and extends about stent graft 60. Optionally, stent graft 60 can be secured by an apex clasp (not shown), as discussed above, at proximal end 70 of stent graft 60. Control lumen 102, outer control tube 106 and an apex clasp, if present, can be controlled at handle 96 to which they are all connected. An introducer sheath (not shown) extends about inner sheath 112, stent graft 60, outer control tube 106 and control lumen 102, and is in interfering relation with nose cone 104 prior to deployment of inner sheath 112 and stent graft 60.

System 100 is particularly suitable for use where an endoluminal prosthesis is not implanted by directing the prosthesis through an femoral artery of a patient (transfemoral access), but alternatively introduced through the left ventricle of a patient's heart (transapical access). In this embodiment, introducer sheath 92, containing stent graft 60, is directed through the left ventricle of a patient's heart until stent graft 60 spans the diseased portion of an artery, such as an aneurysm at the ascending aorta. Control lumen 102 is then further advanced, thereby causing nose cone 104 to further advance and pull inner sheath 112 with it, thereby exposing and deploying stent graft 60. Supporting wires provide longitudinal resistance to prevent movement of stent graft 60 during deployment. Once stent graft 60 is fully exposed, or deployed, outer control tube 106 is advanced to release supporting wires from loops within stent graft 60, as described above. System 100 can then be retracted through stent graft 60 and removed from the patient.

Figure 21A:
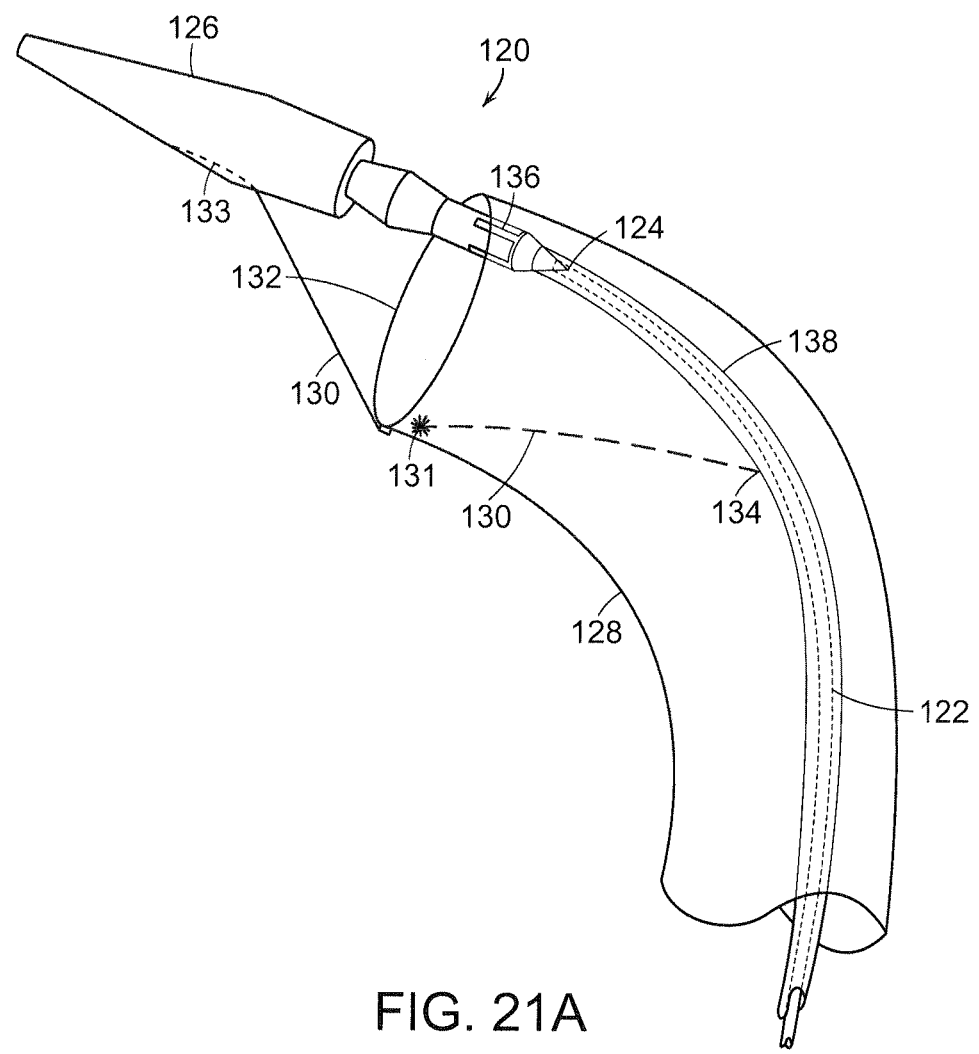
FIG. 21A depicts an alternative embodiment of the invention, that includes at least one suture and an apex clasp.
Figure 21B:
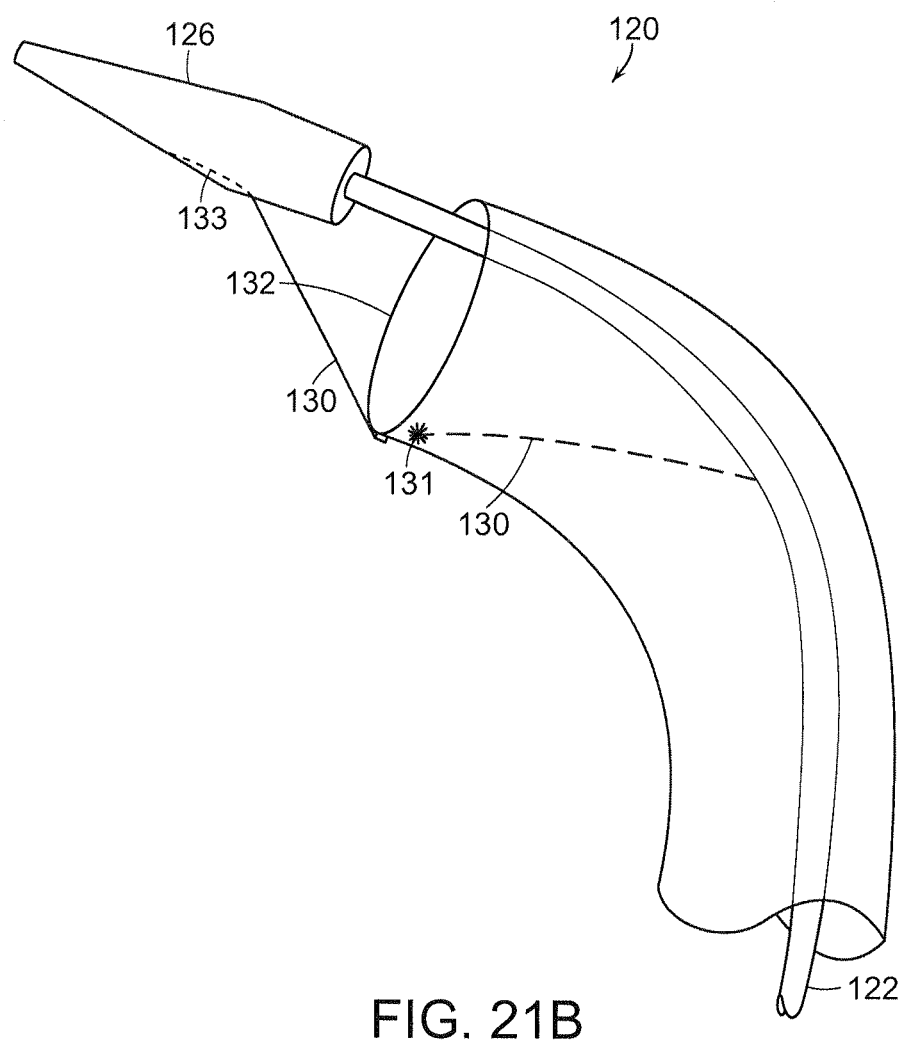
FIG. 21B depicts another alternative embodiment of the invention, that includes at least one suture.

In still another embodiment, shown in FIG. 21A, system 120 includes control lumen 122 having distal end 124 and nose cone 126 fixed at distal end 124. Stent graft 128 extends about control lumen 122. At least one suture 130 extends from nose cone 126 to proximal end 132 of stent graft 128, and from stent graft 128 to a fixed location 134 on control lumen 122. Suture 130 is releaseable from stent graft 128 by remote activation, whereby suture 130 separates from nose cone 126 to thereby deploy stent graft 128. In one embodiment, nose cone 126 includes longitudinal slot 133 at a distal end of suture 130 in interfering relation with slot 133, whereby increased tension in suture 130 causes suture 130 to come free of longitudinal slot 133 and, therefore, from nose cone 126. Further, suture 130 includes an expanded portion 131, such as knot, in interfering relation with the loop or the hole, not shown, whereby longitudinal movement of portion 130 of proximal end 132 of stent graft 128 back toward the surgeon is prevented while distal end of suture 130 is in interfering relation with nose cone 126. When suture 130 is withdrawn from the longitudinal slot, suture can be withdrawn through the loop or the hole to thereby release proximal end 132 of stent graft 128. Apex clasp 136 is controlled by outer control tube 138. Alternatively, as shown in FIG. 21B, system 120 locks apex clasp 136 and outer control tube 138. The suture employed in the systems of FIGS. 21A and 21B can be a thread that includes a biocompatible material, such as a suture gut, or a metal (e.g., wire) that includes stainless steel or a shape memory alloy.

In another embodiment, shown in FIGS. 22A and 22B, inner sheath 210 about stent graft 60 and extending from inner sheath liner 212 includes proximal perforated portion 214 that defines through-holes. The through-holes can be defined by a mesh or fabric of perforation portion 214 as shown in FIG. 22A or as distinct openings, such as longitudinal through-hole opening 216 shown in FIG. 22B, that extend substantially parallel to a major axis of inner sheath 210. Typically, the through-holes have a diameter equal to or greater than about 25 mm. The through-holes permit relatively continuous blood flow through stent graft 60 from aortic valve 218 through aortic arch 220 in the direction shown by arrows 222 during implantation of stent graft 60. Inner sheath of the invention defining through-holes can also be employed at other intended surgical sites, such as the mesenteric artery or the celiac artery.

Systems, stent grafts and delivery devices and components of systems, stent grafts and delivery devices as described in U.S. application Ser. No. 10/784,462, filed on Feb. 23, 2004; Ser. No. 10/884,136, filed on Jul. 2, 2004; Ser. No. 11/348, 176, filed on Feb. 6, 2006; Ser. No. 11/353,927, filed on Feb. 13, 2006; Ser. No. 11/449,337, filed on Feb. 13, 2006; Ser. No. 11/699,700, filed on Jan. 30, 2007; Ser. No. 11/699,701, filed on Jan. 30, 2007; Ser. No. 11/700,609, filed on Jan. 30, 2007; Ser. No. 11/700,510, filed on Jan. 31, 2007; Ser. No. 11/701, 867, filed on Feb. 1, 2007; Ser. No. 11/828,675, filed on Jul. 26, 2007; Ser. No. 11/828,653, filed on Jul. 26, 2007; Ser. No. 12/137,592, filed on Jun. 12, 2008; Ser. No. 11/701,876, filed on Feb. 1, 2007; 61/164,545, filed on Mar. 30, 2009; and Ser. No. 12/459,387, filed on Jun. 30, 2009, the teachings of all of which are hereby incorporated by reference in their entirety, can be employed in the systems, stent grafts and delivery devices described herein.

The teachings of all patents, published applications and references cited herein are incorporated by reference in their entirety.

Equivalents

While this invention has been particularly shown and described with references to example embodiments thereof, it will be understood by those skilled in the art that various changes in form and details may be made therein without departing from the scope of the invention encompassed by the appended claims.

What is claimed is:

1. A system for implanting a prosthesis, comprising:
   a) an arcuate control lumen, the arcuate control lumen having a superior side, an inferior side, and a distal end;
   b) a nose cone fixed at the distal end of the arcuate control lumen; and
   c) at least one supporting wire having a fixed proximal end and a free distal end opposite the fixed proximal end, wherein only the proximal end is fixed, and wherein the at least one supporting wire extends along the inferior side of the arcuate control lumen and splays away from the arcuate control lumen, wherein the free distal end of the at least one supporting wire is flexible and arcuate, and arcs toward the arcuate control lumen.

2. The system of claim 1, further including an outer control tube slideable along the arcuate control lumen, wherein the fixed proximal end of the at least one supporting wire is fixed at one end to the outer control tube.

3. The system of claim 2, wherein the fixed proximal end of the at least one supporting wire is fixed to the outer control tube proximal to the nose cone to thereby form a fixed end and the free distal end is distal to the fixed end and is proximate to the nose cone.

4. The system of claim 3, further including an apex clasp at an end of the outer control tube and slideable along the control lumen with movement of the outer control tube.

5. The system of claim 4, further including a stent graft extending about the outer control tube and the at least one supporting wire, the stent graft including a proximal end at the clasp and a distal end that is proximal to the clasp.

6. The system of claim 5, wherein the stent graft includes at least one clasp stent defining at least one exposed portion that is releasably secured to the clasp.

7. The system of claim 6, wherein the stent graft includes for each of the at least one supporting wire, a loop within the stent graft that releasably secures the free distal end of each respective at least one supporting wire.

8. The system of claim 7, wherein the stent graft includes a crown stent at the proximate end of the stent graft.

9. The system of claim 8, wherein the crown stent is secured to an interior portion of a graft portion of the stent graft.

10. The system of claim 9, wherein the crown stent is between the clasp stent and the proximal end of the stent graft.

11. The system of claim 5, wherein the stent graft further includes at least one radiopaque marker.

12. The system of claim 1, further including a pusher support tube distal or proximal to the fixed distal end of the at least one supporting wire and slideable along the arcuate control lumen.

13. The system of claim 12, further including an outer control tube slideable along the arcuate control lumen, wherein the fixed proximal end of the at least one supporting wire is fixed at one end to the outer control tube.

14. The system of claim 13, further including an apex clasp at an end of the outer control tube and slideable along the control lumen with movement of the outer control tube.

15. The system of claim 1, wherein the at least one supporting wire is formed of at least one member selected from the group consisting of a metal, an alloy and a polymer.

16. The system of claim 15, wherein the metal includes stainless steel.

17. The system of claim 15, wherein the alloy includes a shape memory alloy.

18. The system of claim 17, wherein the shape memory alloy includes a nickel titanium alloy.

19. The system of claim 1, wherein the system includes at least two supporting wires.

20. The system of claim 19, wherein the system includes two supporting wires.

21. The system of claim 1, wherein the fixed proximal end of the at least one supporting wire is fixed to the arcuate control lumen proximate to the nose cone, and wherein the free distal end of the at least one supporting wire is proximal to the fixed proximal end.

22. The system of claim 21, further including an inner sheath that is fixed to the nose cone and extends proximally from the nose cone about the at least one supporting wire.

23. The system of claim 22, further including a stent graft extending about the control lumen and the at least one supporting wire and within the inner sheath.

24. The system of claim 23, wherein the stent graft includes at least one loop within the stent graft that releasably secures the free distal end of each respective at least one supporting wire.

25. The system of claim 1, further including an inner sheath with a distal portion, and wherein the nose cone defines a proximal cavity into which the distal portion of the inner sheath fits, whereby relative motion of the nose cone and the inner sheath releases the distal end of the inner sheath from the proximal cavity.

26. The system of claim 25, wherein the nose cone is retractable within the inner sheath after release of the inner sheath.

27. The system of claim 26, further including a stent graft within the inner sheath, inner sheath and the nose cone are retractable relative to the stent graft.

28. The system of claim 27, wherein the stent graft includes a loop inside the stent graft that releasably secures a respective at least one supporting wire, whereby movement of the loop along the at least one supporting wire is restricted.

29. The system of claim 26, whereby the stent graft is deployed by joint retraction of the inner sheath and the nose cone.

30. The system of claim 1, wherein the fixed proximal end of the at least one supporting wire is fixed to the arcuate control lumen.

31. The system of claim 1, further including a buttress having a proximal end and a distal end, the proximal end of the buttress fixed to the distal end of the arcuate control lumen proximal to the nose cone and wherein the fixed proximal end of the at least one supporting wire is fixed to the distal end of the buttress.

32. A system for implanting a prosthesis, comprising:
   a) an arcuate control lumen, the arcuate control lumen having a superior side, an inferior side and a distal end;
   b) a nose cone fixed at the distal end of the arcuate control lumen;
   c) an flexible inner sheath extending about the arcuate control lumen that defines a distal opening at a distal end of the inner sheath, wherein the nose cone is retractable within the inner sheath; and
   d) at least one supporting wire having a fixed proximal end and a free distal end, wherein only the proximal end is fixed, and wherein the at least one supporting wire extends along the inferior side of the arcuate control lumen and splays away from the arcuate control lumen and the free distal end of at least one of the supporting wires is flexible and arcuate, and arcs towards the arcuate control lumen.

33. The system of claim 32, wherein the inner sheath is a flexible inner sheath and the nose cone defines a cavity within which the distal end of the flexible inner sheath can fit, and which will release the distal end of the flexible inner sheath upon retraction of the distal end of the flexible inner sheath from the cavity of the nose cone, the nose cone being retractable within the flexible inner sheath after release of the distal end of the flexible inner sheath from the cavity.

34. The system of claim 32, wherein the fixed proximal end of the at least one supporting wire is fixed to the arcuate control lumen.

35. The system of claim 32, further including a buttress having a proximal end and a distal end, the proximal end of the buttress fixed to the distal end of the arcuate control lumen proximal to the nose cone and wherein the fixed proximal end of the at least one supporting wire is fixed to the distal end of the buttress.

* * * * *

UNITED STATES PATENT AND TRADEMARK OFFICE
CERTIFICATE OF CORRECTION

PATENT NO. : 9,101,506 B2  Page 1 of 1
APPLICATION NO. : 12/723431
DATED : August 11, 2015
INVENTOR(S) : Samuel Arbefeuille et al.

It is certified that error appears in the above-identified patent and that said Letters Patent is hereby corrected as shown below:

In The Claims
In Column 14, Claim 2, Line 31, before "to the outer" - delete "at one end"
In Column 14, Claim 3, Line 35, after "fixed end" - insert -- , --
In Column 14, Claim 4, Line 38, before "end of the" - delete "an" and insert -- a distal --
In Column 14, Claim 8, Line 52, after "stent at the" - delete "proximate" and insert -- proximal --
In Column 14, Claim 12, Line 61, after "support tube" - delete "distal or" and;
    after "to the fixed" - delete "distal" and insert -- proximal --
In Column 14, Claim 13, Line 67, after "is fixed" - delete "at one end"
In Column 15, Claim 14, Line 2, after "at" - delete "an" and insert -- a distal --
In Column 15, Claim 21, Line 19, after "control lumen" - delete "proximate" and insert -- proximal --
In Column 15, Claim 22, Line 23, after "sheath that is" - insert -- releasably --
In Column 15, Claim 27, Line 42, after "within the inner sheath," - insert -- and wherein the --
In Column 16, Claim 29, Line 1, after "claim 26," - delete "whereby" and insert -- wherein --

Signed and Sealed this
Fifth Day of January, 2016

Michelle K. Lee
*Director of the United States Patent and Trademark Office*